(12) United States Patent
Ciaccio

(10) Patent No.: US 8,386,014 B2
(45) Date of Patent: Feb. 26, 2013

(54) SYSTEMS AND METHODS FOR IMPLEMENTING HEART GEOMETRICAL MEASUREMENTS

(75) Inventor: Edward J. Ciaccio, Cherry Hill, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1253 days.

(21) Appl. No.: 12/144,310

(22) Filed: Jun. 23, 2008

(65) Prior Publication Data

US 2009/0099563 A1 Apr. 16, 2009

Related U.S. Application Data

(60) Provisional application No. 60/945,496, filed on Jun. 21, 2007.

(51) Int. Cl.
*A61B 5/05* (2006.01)
(52) U.S. Cl. ........ 600/411; 600/407; 600/427; 600/439; 600/410; 382/128
(58) Field of Classification Search .................. 600/410, 600/409, 411, 508, 479, 515, 518
See application file for complete search history.

(56) References Cited

U.S. PATENT DOCUMENTS

| | | | |
|---|---|---|---|
| 5,718,241 A | 2/1998 | Ben-Haim et al. | |
| 5,772,604 A | 6/1998 | Langberg et al. | |
| 5,954,665 A | 9/1999 | Ben-Haim | |
| 6,236,883 B1* | 5/2001 | Ciaccio et al. | 600/515 |
| 6,760,620 B2 | 7/2004 | Sippens Groenewegen | |
| 6,847,839 B2 | 1/2005 | Ciaccio et al. | |
| 6,868,287 B1* | 3/2005 | Rosen et al. | 607/9 |
| 7,245,962 B2 | 7/2007 | Ciaccio et al. | |
| 2003/0023130 A1* | 1/2003 | Ciaccio et al. | 600/12 |
| 2005/0038333 A1* | 2/2005 | Sra | 600/374 |

OTHER PUBLICATIONS

Ashikaga, et al., 2005, "Electromechanical Analysis of Infarct Border Zone in Chronic Myocardial Infarction," *Am. J. Physiol. Heart Circ. Physiol.*, vol. 289: p. H1099-H1105.
Baba, et al., 2005, "Remodeling in cells from different regions of the reentrant circuit during ventricular tachycardia," *Circulation*, vol. 112: p. 2386-2396.
Cabo, et al., 1994, "Wave-front curvature as a cause of slow conduction and block in isolated cardiac muscle," *Circ. Res.*, vol. 75: p. 1014-1028.
Cabo, et al., 2003, "Electrical remodeling of the epicardial border zone in the canine infarcted heart: a computational analysis," *Am. J. Physiol. Heart Circ. Physiol.*, vol. 284: p. H372-H384.
Cabo, et al., 2006, "Heterogeneous gap junction remodeling in reentrant circuits in the epicardial border zone of the healing canine infarct," *Cardiovasc Res*, vol. 72: p. 241-249.

(Continued)

*Primary Examiner* — Tse Chen
*Assistant Examiner* — Joel F Brutus
(74) *Attorney, Agent, or Firm* — Baker Botts LLP

(57) ABSTRACT

In some embodiments, the disclosed subject matter provides a method of identifying the source of arrhythmia, e.g. reentrant ventricular tachycardia, in a patient. In other embodiments, the disclosed subject matter provides a method for treating or preventing reentrant ventricular tachycardia in a patient. In still other embodiments, the disclosed subject matter provides systems for identifying the location of a candidate ablation site in a patient. In some embodiments, the patient has suffered from a myocardial infarction or has undergone structural remodeling of the heart caused by, e.g., cardiac fibrosis or the presence of dense trebeculation, resulting in nonviable areas with border zones (BZ).

20 Claims, 13 Drawing Sheets

OTHER PUBLICATIONS

Cabo, et al., 2006, "Heterogeneous gap junction remodeling in reentrant circuits in the epicardial border zone of the healing canine infarct: a computational study," *Am J Physiol Heart Circ Physiol*, vol. 291: p. H2606-H2616.

Cappato, et al., 2005, "Worldwide survey on the methods, efficacy, and safety of catheter ablation for human atrial fibrillation," *Circulation*, vol. 111: p. 1100-1105.

Ciaccio, et al., 2001, "Relationship between sinus rhythm activation and the reentrant ventricular tachycardia isthmus," *Circulation*, vol. 104: p. 613-619.

Ciaccio, et al., 2001, "Static relationship of cycle length to reentrant circuit geometry," *Circulation*, vol. 104: p. 1946-1951.

Ciaccio, et al., 2004, "Localization of the isthmus in reentrant circuits by analysis of electrograms derived from clinical noncontact mapping during sinus rhythm and ventricular tachycardia," *J. Cardiovascular Electrophysiology*, vol. 15: p. 27-36.

Ciaccio, et al., 2004, "Sinus rhythm electrogram shape measurements are predictive of the origins and characteristics of multiple reentrant ventricular tachycardia morphologies," *J. Cardiovascular Electrophysiology*, vol. 15: p. 1293-1301.

Ciaccio, et al., 2005, "Ventricular tachycardia duration and form are associated with electrical discontinuities bounding the core of the reentrant circuit," *J. Cardiovascular Electrophysiology*, vol. 16: p. 646-654.

Ciaccio, et al., 2007, "Model of reentrant ventricular tachycardia based on infarct border zone geometry predicts reentrant circuit features as determined by activation mapping," *Heart Rhythm Society*, vol. 4, No. 8: p. 1034-1044.

Clayton, et al. 2002, "Computational framework for stimulating the mechanisms and ECG of re-entrant ventricular fibrillation," *Physiol Meas*, vol. 23: p. 707-726.

Coronel, 2007, "Myths, metaphors, and mathematical models," *Heart Rhythm*, vol. 4: p. 1046-1047.

Costeas, et al., 1997, "Mechanisms causing sustained ventricular tachycardia with multiple QRS morphologies: results of mapping studies in the infarcted canine heart," *Circulation*, vol. 96: p. 3721-3731.

Cox, et al., 1996, "An 8 1/2-year clinical experience with surgery for atrial fibrillation," *Ann. Surg.*, vol. 224, No. 3: p. 267-273.

De Bakker, et al., 2005, "Three-dimensional anatomic structure as substrate for ventricular tachycardia/ventricular fibrillation," *Heart Rhythm*, vol. 2, No. 7: p. 777-779.

Dillon, et al., 1988, "Influences of anisotropic tissue structure on reentrant circuits in the epicardial border zone of subacute canine infarcts," *Circ. Res.*, vol. 63: p. 182-206.

Faris, et al., 2003, "Novel technique for cardiac electromechanical mapping with magnetic resonance imaging tagging an an epicardail electrode sock," *Ann Biomed Eng*, vol. 31: p. 430-440.

Fast, et al., 1997, "Role of wavefront curvature in propagation of cardiac impulse," *Cardiovascular Research*, vol. 33: p. 258-271.

Frost and Sullivan, 2006, U.S. Cardiac Rhythm Management Markets, http://www.marketresearch.com/product/display.asp?productid=1278098.

Garan, 1996, "A perspective on the ESVEM trial and current knowledge: catheter ablation for ventricular tachyarrhythmias," *Progress in Cardiovascular Diseases*, vol. 38: p. 457-462.

Janse, et al., 1998, "Animal models of cardiac arrhythmias," *Cardiovasc Res*, vol. 39: p. 165-177.

Kim, et al., 1999, "Relationship of MRI Delayed Contrast Enhancement to Irreversible Injury, Infarct Age, and Contractile Function," *Circulation*, vol. 100: p. 1992-2002.

Kleber, et al., 2004, "Basic mechanisms of cardiac impulse propagation and associated arrhythmias," *Physiol. Rev.*, vol. 84: p. 431-488.

Kogan, et al., 1992, "Excitation Wave Propagation Within Narrow Pathways: Geometric Configurations Facilitating Unidirectional Block and Reentry," *Physica. D.*, vol. 59: p. 275-296.

MacLeod RS, Johnson CR., 1993, "Map3d: Interactive Scientific Visualization for Bioengineering Data," IEEE Engineering Medicine Biology Society 15th Annual International Conference: p. 30-31, 19.

Miragoli, et al., 2006, "Electrotonic modulation of cardiac impulse conduction by myofibroblasts," *Circ Res*, vol. 98: p. 801-810.

Percival and Walden, 1993 "Spectral Analysis for Physical Applications," Cambridge University Press, Great Britain.

Perstov, et al., "Spiral waves of excitation underlie reentrant activity in isolated cardiac muscle," *Circ Res*, vol. 72: p. 631-650.

Peters, et al., 1997, "Disturbed connexin43 gap junction distribution correlates with the location of reentrant circuits in the epicardial border zone of healing canine infarcts that cause ventricular tachycardia," *Circulation*, vol. 95: p. 988-996.

Ramza, et al., 1990, "Cellular mechanism of the functional refractory period in ventricular muscle," *Circulation Research*, vol. 66: p. 147-162.

Sampson, et al., 2002, "Interplay of ionic and structural heterogeneity on functional action potential duration gradients: Implications for arrhythmogenesis," *Chaos*, vol. 12: p. 819-828.

Spach, et al., 2004, "Cell size communications: role in structural and electrical development and remodeling of the heart," *Heart Rhythm*, vol. 1: p. 500-515.

Wit, et al., 1982, "Electrophysiologic mapping to determine the mechanism of experimental ventricular tachcardia initiated by premature impulses. Experimental approach and initial results demonstrating reentrant excitation," *Am. J. Cardiol.*, vol. 49: p. 166-185.

Wit, 2006, "Ablation of ventricular tachycardia: does anyone have any new ideas?" *Heart Rhythm*, vol. 3: p. 198-200.

* cited by examiner

Nonsustained
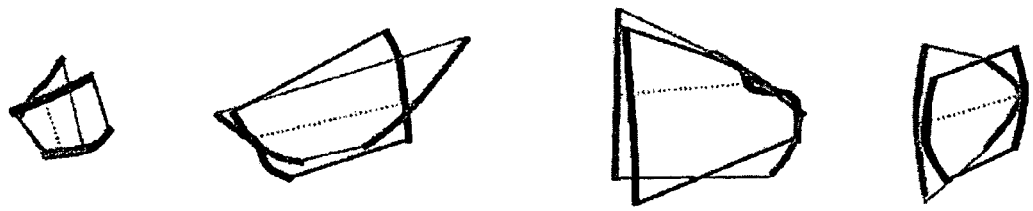
Sustained
1cm
FIG. 8

FIG. 9 Principles of Wavefront Curvature

FIG. 10 Equation to Predict Rapid Conduction Due to Curvature ρ

FIG. 11 Algorithm for heart geometry chart

SYSTEMS AND METHODS FOR IMPLEMENTING HEART GEOMETRICAL MEASUREMENTS

CROSS REFERENCE TO RELATED APPLICATIONS

This application claims priority to U.S. Provisional Application No. 60/945,496 entitled "Heart Geometrical Measurements" filed on Jun. 21, 2007, the entirety of which is explicitly incorporated by reference herein.

STATEMENT REGARDING FEDERALLY-SPONSORED RESEARCH

This invention was made with government support under National Institutes of Health-National Heart, Lung and Blood Institute (NIH-NHLBI) Intramural grant no. Z01-HL4004609 and NIH-NHLBI Program Project grant no. HL30557. The government has certain rights in the invention.

BACKGROUND

Postinfarction reentrant ventricular tachycardia is an important clinical problem, yet locating the circuit can be problematic (Wit A L. *Heart Rhythm* 2006; 3:198-200; Garan H. *Progress in Cardiovascular Diseases* 1996; 38:457-462). Electrical activation mapping, which requires induction of the clinical ventricular tachycardia in the patient, is currently used for pinpointing reentrant circuit location. However, this procedure is often time-consuming and is limited by the fact that clinical tachycardia cannot always be induced and/or it may not be well-tolerated hemodynamically by the patient. Furthermore, in some cases, the relevant clinical reentrant ventricular tachycardia that the patient experiences cannot be induced during electrophysiologic study, in which case it cannot be accurately mapped. Therefore, alternative methods for identifying reentrant circuit location are needed.

In canine postinfarction hearts, the reentrant circuit isthmus has been shown to overlap the thinnest infarct border zone (BZ), and functional block lines tend to coincide with sharper transitions to thicker tissue about the isthmus (Wit A L, et al. *Am J Cardiol* 1982; 49:166-185; Peters N S, et al. *Circulation* 1997; 95:988-996). Both the isthmus and the functional block lines tend to remain approximately constant in location during any particular reentrant circuit morphology (Ciaccio E J, et al. *J Cardiovasc Electrophysiol.* 2004; 15:1293-1301; Ciaccio E J. *J Cardiovascular Electrophysiology* 2005; 16:646-654).

When multiple reentrant circuit morphologies are inducible in the canine infarct BZ, it has been observed that the isthmus location of most or all of the morphologies coincide, with a difference in isthmus entrance and exit points being the distinguishing characteristic (Ciaccio E J, et al. *J Cardiovasc Electrophysiol.* 2004; 15:1293-1301; Ciaccio E J. *J Cardiovascular Electrophysiology* 2005; 16:646-654; and Costeas C. et al. *Circulation.* 1997; 96:3721-3731). Development of a geometric model relating border zone (BZ) structure to reentry conduction characteristics would allow the prediction of reentrant circuit pattern and characteristics from imaging data of the infarct and border zone, as well as identification of the isthmus and candidate ablation sites in postinfarction patients and in other patients with structural remodeling of heart tissue causing nonviable areas with border zones (BZ) about which recurrent ventricular tachycardia can arise. A need therefore remains for development of such a geometric model.

SUMMARY

Systems and methods for implementing heart geometrical measurements are disclosed herein.

In some embodiments, the disclosed subject matter provides a method of identifying the source of arrhythmia, e.g. reentrant ventricular tachycardia in a patient, comprised of obtaining one or more image of the region of the patient's heart; identifying a border zone (BZ); calculating the thickness of the BZ; constructing a three-dimensional thickness map by measuring the thickness of said border zone at multiple points so that a sufficient spatial resolution is obtained, and determining a local spatial gradient ($\Delta T$) of said thickness over two or more locations in said BZ; and using said thickness and $\Delta T$ to determine the reentry isthmus location and one or more candidate ablation sites. In one embodiment, the thickness is calculated as the straight line distance between an infarct or other structurally remodeled surface to the heart surface. In another embodiment, the thickness is calculated as the straight line distance between edges of the infarct or other structurally remodeled surface when that surface is three-dimensional. In some embodiments, the method further comprising performing ablation of said one or more candidate ablation sites.

In some embodiments, the patient has suffered from a myocardial infarction or has undergone structural remodeling of the heart caused by, e.g., cardiac fibrosis or the presence of dense trebeculation, resulting in nonviable areas with border zones (BZ).

In some embodiments, the disclosed subject matter provides a method for treating, preventing, and/or inhibiting postinfarction reentrant ventricular tachycardia in a patient, comprising obtaining one or more image of the patient's heart; identifying a border zone (BZ); calculating the thickness of the BZ; constructing a three-dimensional thickness map by measuring the thickness of said border zone at multiple points so that a sufficient spatial resolution is obtained, and determining a local spatial gradient ($\Delta T$) of said thickness over two or more locations in said BZ; using said thickness and $\Delta T$ to determine the reentry isthmus location and one or more candidate ablation sites; and performing ablation of said one or more candidate ablation sites.

In one embodiment, the thickness is calculated as the straight line distance between an infarct or other structurally remodeled surface to the heart surface. In another embodiment, the thickness is calculated as the straight line distance between edges of the infarct or other structurally remodeled surface when that surface is three-dimensional.

In some embodiments, the patient has suffered from a myocardial infarction or has undergone structural remodeling of the heart caused by, e.g., cardiac fibrosis or the presence of dense trebeculation, resulting in nonviable areas with border zones (BZ).

Obtaining images can comprise the use of imaging technology capable of achieving 1 mm resolution or less, e.g., MRI. In one embodiment, measuring thickness comprises determining the thickness of said border zone with 1 mm or higher precision.

In another embodiment, the methods and systems of the disclosed subject matter are used to distinguish patients in which ventricular tachycardia originates from a sustained or nonsustained reentrant circuit or from a nonreentrant (focal) source. In this embodiment, said detection is important to determine the type of treatment (use and extent of ablation therapy as compared with drug treatments, surgery, or other means of therapy).

In another embodiment, obtaining high-resolution images comprises the use of imaging technology capable of achieving 1 mm resolution or less, for example, magnetic resonance imaging (MRI). In yet another embodiment, measuring the thickness comprises determining the thickness of said border zone with 1 mm or higher precision.

In still other embodiments, the disclosed subject matter provides a system for identifying the location of a candidate ablation site in a patient, e.g., a myocardial infarct patient, the system comprising a processor, image acquisition means for obtaining images, e.g., high-resolution (1 mm or higher), of a patient's heart operatively coupled to the processor, and a memory operatively coupled to the processor, the memory storing program instructions that when executed by the processor, cause said processor to utilize said image acquisition means for obtaining high-resolution images to: obtain one or more images of a patient's heart; display the images on a screen; measure a thickness of border zones; determine a local spatial gradient ($\Delta T$) of said thickness over two or more locations in said border zones; plot said thickness and thickness gradient values on three-dimensional maps; and locate estimated positions of reentrant circuits and actual conduction block during reentrant ventricular tachycardia.

In another embodiment, the system further comprises analyzing means, which analyzing means operatively coupled with said image acquisition means for analyzing whether the geometry and location of reentrant circuits indicate predisposition to ventricular tachycardia in the patient, and if so, whether the arrhythmia will be nonsustained or sustained.

In some embodiments, the disclosed subject matter provides methods and systems to pinpoint the location of functional lines of conduction block during ventricular tachycardia at the lateral edges of the isthmus. The method is based on determining areas where areas of thinnest border zone (<~1 mm) are adjacent to much thicker areas and in one embodiment is based upon the derivation shown in Equations 4-9 and in particular Equation 9, as set forth herein. It is estimated that during ventricular tachycardia, functional conduction block will occur at the boundary between the two regions.

In other embodiments, the disclosed subject matter provides methods and systems for determining areas of slow conduction which occur at the entrance and exit points of the isthmus, based upon determining areas where the change in border zone thickness with distance is more gradual than at the lateral edges of the isthmus. It is at these points that the electrical and geometric properties of the tissue are conductive to the activation wavefront entering the isthmus (at the entrance point) and exiting the isthmus (at the exit point). In one embodiment, based on the entrance and exit points, the direction of travel of the activating wavefront through the isthmus can be ascertained.

In other embodiments, the disclosed subject matter provides methods and systems for determining the precise location of the isthmus of the reentrant circuit which is bounded by functional conduction block at the lateral edges and by entrance and exit points at other edges, which in conjunction with knowing the orientation that the activation wavefront will propagate during reentrant ventricular tachycardia, can be used to determine a best or optimal line to make an ablation lesion during clinical study of the patient's heart condition.

In further embodiments, the disclosed subject matter provides methods and systems for determining the path of least resistance about which the outer loops of the reentrant circuit will form during reentrant ventricular tachycardia comprising determining pathways of highest conduction velocity, and therefore least resistance (using, for example, Equation 1), as set forth herein, along which the outer loops of the reentrant circuit will form during ventricular tachycardia, which, in one embodiment, is based on the derivation shown in Equations 10-15, and specifically Equation 15. The areas where fast conduction velocity will occur are identified based on the gradient $\Delta T$. Rapid conduction will occur along pathways of small, uniform gradient $\Delta T$ in the general direction from the isthmus to outer circuit and vice versa.

In still other embodiments, the disclosed subject matter provides methods and systems for creating a map which estimates the pattern of activation during reentry using MRI or other imaging means, during the normal heart rhythm or other rhythm, without the need for electrophysiologic study of the patient involving the induction of clinical ventricular tachycardia followed by electrical activation mapping. The map that is generated by imaging means shows the estimated locations of functional lines of conduction block, areas of slow conduction at entrance and exit points, the isthmus boundaries along these regions, and areas of rapid conduction along which the loops of the reentrant circuit pass (see FIGS. 12 and 13).

In additional embodiments, the disclosed subject matter provides a method to ablate the heart based upon the estimated location of functional conduction block and entrance and exit points to the isthmus. The method comprises determining the shortest straight line distance between two estimated arcs of functional conduction block locations, that is positioned in such a way so as to interrupt conduction in the constrained region between the isthmus entrance and exit, and ablating along this line. The feasibility of ablating the heart between arcs of functional conduction block to prevent reinductance of reentrant ventricular tachycardia has been validated (Ciaccio E J et al. *J Cardiovasc Electrophysiol.* 2004 Nov; 15(11):1293-301).

BRIEF DESCRIPTION OF THE DRAWINGS

The accompanying drawings, which are incorporated and constitute part of this disclosure, illustrate some exemplary embodiments of the disclosed subject matter.

FIGS. 1A-1C show histology measurement. Adjacent wax sections were stained with Masson's trichrome stain to distinguish infarcted from surviving myocytes. FIGS. 1D-F show MRI measurements. FIG. 1E illustrates that ex-vivo MR scanning provides a view of the heart slice from above (base to apex) including the infarct region (white).

FIG. 2A is a diagram of the extrastimulation cycle leading to reentry. FIG. 2B is a schematic of the relationship between BZ thickness (Z-axis) and wavefront curvature when propagation within the reentrant circuit is in parallel to the plane of the epicardial surface (XY), in accordance with an embodiment of the disclosed subject matter.

FIG. 3A depicts wavefront curvature as a circular arc. FIG. 3B is a geometrical configuration for calculating wavefront curvature due to BZ thickness change. FIG. 3C depicts a method to determine the maximum thickness change ($\Delta T_{max}$) in proximity to a particular computational node.

FIGS. 4A-B shows activation during sinus rhythm and ventricular tachycardia. Thin lines separating grayscale denote isochrones. FIG. 4C shows BZ thickness T determined from histology slides. FIG. 4D. shows the thickness gradient $\Delta T_{max}$. FIG. 4E illustrates $\rho_{max}$ (maximum degree of wavefront curvature) estimated from Equation 9. Overlaid are the locations of estimated (gray) and actual (black) lines of block (also in FIGS. 5-7). FIG. 4F is the multielectrode grid.

FIGS. 5A-B shows activation during sinus rhythm and ventricular tachycardia. FIGS. 5C-D shows BZ thickness T determined from MR images. FIGS. 5E-F. shows thickness gradient $\Delta T_{max}$. FIGS. 5G-H illustrates the maximum degree of wavefront curvature $\rho_{max}$ estimated from Equation 9. Estimated block lines computed from panel G (gray), and actual block lines determined from the ventricular tachycardia activation map in panel B (black) are overlaid on the maps in panels C, E and G (also in FIGS. 6-7).

FIG. 8 illustrates overlap of estimated isthmus location (from maps derived using Equation 9) with actual isthmus location (from tachycardia activation map), in six experiments with inducible reentrant ventricular tachycardia, in accordance with an embodiment of the disclosed subject matter.

DETAILED DESCRIPTION

Figure 1:
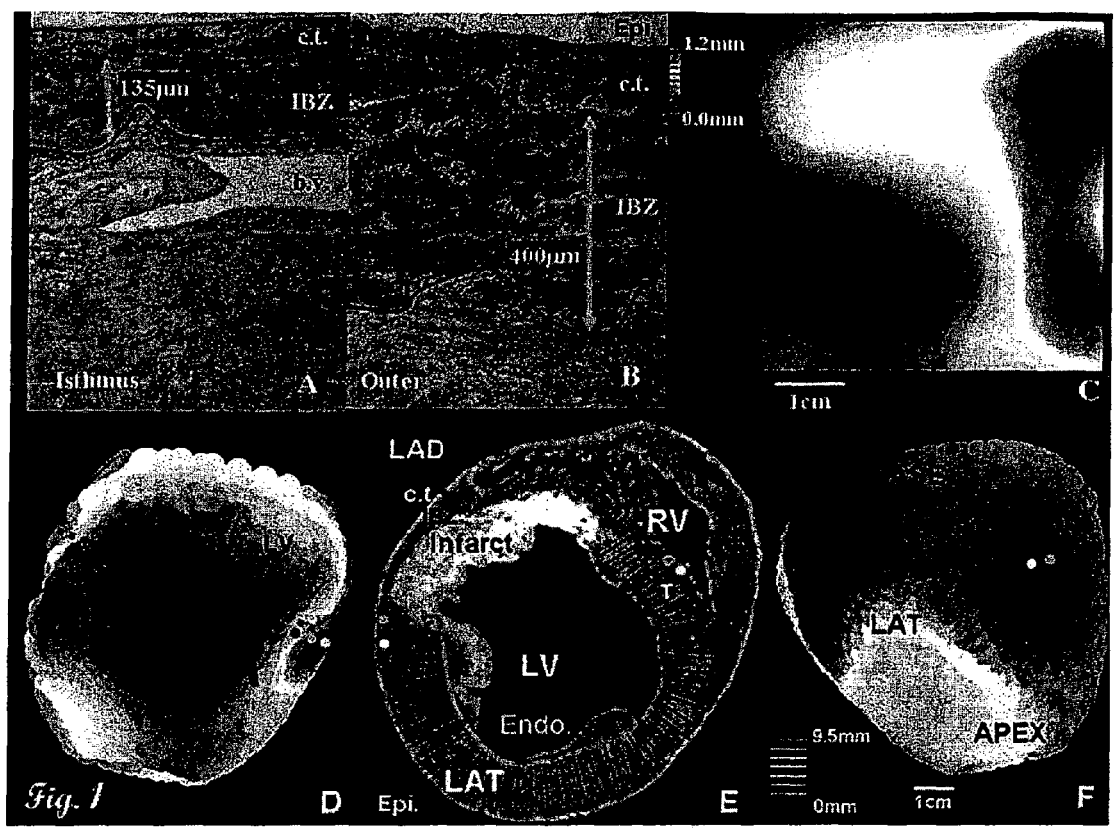
FIGS. 1A-F show histology and MRI images which were used to measure BZ thickness in accordance with an embodiment of the disclosed subject matter.

The disclosed subject matter provides a new geometric model describing the relationship between border zone (BZ), e.g., infarct border zone (IBZ), geometry and wavefront propagation in reentrant circuits. Based on the formulation, as described herein, slow conduction and block during reentrant ventricular tachycardia coincide with areas where BZ thickness (T) is minimal and the local spatial gradient in thickness ($\Delta T$) is maximal, so that the degree of wavefront curvature $\rho \propto \Delta T/T$ (Equation 10) is maximal. Regions of fastest conduction velocity can be predicted to coincide with areas of minimum $\Delta T$.

The disclosed subject matter therefore provides non-invasive methods for treating, preventing, and/or inhibiting postinfarction arrhythmia e.g., reentrant ventricular tachycardia, in a patient, e.g., a patient who has suffered from a myocardial infarction, cardiac fibrosis, heavily trabeculated myocardium, or other structural remodeling of the heart tissue causing nonviable areas with border zones (BZ). By using a geometric model relating BZ structure to reentry conduction characteristics, the reentrant circuit pattern and characteristics can be predicted from imaging data of the border zone. Using cardiac imaging technology which provides images of the heart in sufficient resolution, including, but not limited to, magnetic resonance technology (MRI), the geometric formulation, as described herein, can be used to pinpoint the isthmus and candidate ablation sites in patients with recurrent ventricular tachycardia arising from myocardial infarction or other structural remodeling including but not limited to cardiac fibrosis or presence of heavily trabeculated myocardium that has caused nonviable areas with border zones (BZ). Ablation can then be used to treat, prevent and/or inhibit reentrant ventricular tachycardia in these patients.

In the context of preventing and/or inhibiting reentrant ventricular tachycardia, a patient who has suffered a myocardial infarct or other structural remodeling of heart tissue that has caused nonviable areas with border zones (BZ) may not have yet suffered arrhythmia e.g., ventricular tachycardia. The disclosed methods may be used to identify whether or not the patient is at risk for developing such arrhythmia, and steps may be taken to prevent and/or inhibit the occurrence of arrhythmia in the patient, e.g., ablation may be performed. The disclosed methods and systems may also be used to estimate the characteristics of the source from which the arrhythmia will arise, e.g., whether the source will be reentrant or focal and the likely duration of episodes of ventricular tachycardia. Such estimates are important to plan clinical therapies.

The disclosed subject matter also provides systems for identifying the location of a candidate ablation site in a patient, e.g., an MI patient or a patient who has suffered cardiac fibrosis, heavily trabeculated myocardium, or other structural remodeling of the heart tissue that has caused nonviable areas with border zones (BZ). In one embodiment, the system comprises a processor, image acquisition means for obtaining images, e.g., high-resolution (1 mm or higher) images, of a patient's heart operatively coupled to the processor, and a memory operatively coupled to the processor, the memory storing program instructions that when executed by the processor, cause said processor to utilize said image acquisition means for obtaining high-resolution data to: obtain images of a patient's heart; display each image on a screen; measure a thickness of border zones; determine a local spatial gradient ($\Delta T$) of said thickness over two or more locations in said border zones; plot said thickness and thickness gradient values on three-dimensional maps; and locate estimated positions of reentrant circuits and actual conduction block during reentrant ventricular tachycardia.

In another embodiment, the system further comprises analyzing means, which analyzing means are operatively coupled with image acquisition means for analyzing whether the geometry and location of reentrant circuits indicate predisposition to ventricular tachycardia in the patient.

In the context of the disclosed subject matter, "ablation" is the process whereby tissue (such as heart tissue) is destroyed by imparting energy. Radiofrequency energy, for example, can be used because it is relatively safe and painless. The cells which die as a result of ablation do not conduct electricity and they are gradually replaced with connective tissue. The connective tissue does not activate though there may be a small amount of electrical conduction through it.

As used herein, "catheter ablation" is the creation of a lesion of the surface of the heart using radiofrequency or other energy source emitted from the end or tip of a tubular device called a catheter that is positioned through a large artery into the ventricular chamber of the heart. Cathether ablation can be used in the methods of the invention.

As used herein, "catheter" means a device composed of a narrow, flexible tube capable of fitting within the confines of a human artery which contains. electrodes for recording electrogram signals and for ablating the heart. As used herein, "catheter tip" means the distal end of the catheter, i.e., the end that is positioned within the ventricular cavity.

In the context of the disclosed subject matter, "activation" means an electrical process whereby cells of the heart (myocytes) activate. They become electrically depolarized in their interiors with respect to the extracellular medium. Through an electromechanical coupling process, this eventually results in contraction of the heart at the areas where the cells are activating.

In the context of the disclosed subject matter, "activation mapping" means determining the time of electrical activation over an area of the heart. This is done by obtaining signals from many locations. When the activation wave passes at a particular recording location, it causes a deflection in the signal obtained from there. This deflection is marked and its time is noted. When this is done for recordings at many locations, a map of activation times can then be constructed. The map shows the timing where the activation wave arrived at the recording sites over one cardiac cycle. Activation maps can be made for any or all cardiac cycles.

In the context of the disclosed subject matter, an "anatomical conduction block" is a conduction block that occurs during all cardiac rhythms. It is not dependent on the frequency of the cardiac cycle or upon intercepting wavefronts.

In the context of the disclosed subject matter, an "arrhythmia" is an irregular heartbeat, e.g., ventricular tachycardia. In the context of the disclosed subject matter, "ventricular tachycardia" means an abnormal heart rhythm in which the heart beats more rapidly than normal, which can be caused by a reentrant circuit. It is a common type of arrhythmia and common after MI or in the presence of other structural remodeling of the heart including presence of cardiac fibrosis or heavily trabeculated myocardium. The patient is often, but not always, aware of ventricular tachycardia as it occurs. The arrhythmia can be life-threatening and can result in fainting or even cardiac arrest due to the insufficient pumping of blood during the arrhythmia.

In the context of the disclosed subject matter, "arrythmogenic tissue" is heart tissue that has the capacity to cause the heart to beat irregularly.

In the context of the disclosed subject matter, a "block" (e.g. a "conduction block") is the cessation of propagation of the activation wavefront.

As used herein, "block lines" means the curvilinear areas on the surface of the heart where the activating wavefront conducts slowly or not at all.

In the context of the disclosed subject matter, a "circuit" is a closed loop, or circular path, about which electricity passes. In the case of cardiac tissue, this is the loop about which the activation wavefront processes. The wavefront travels around a line of conduction block to form the loop. In so doing it travels along pathways of least resistance (highest conduction velocity).

In the context of the disclosed subject matter, "clinical ventricular tachycardia" is the ventricular tachycardia that occurs while a patient undergoes everyday activities. During electrophysiologic study, other ventricular tachycardia morphologies besides clinical ventricular tachycardias may occur during the electrical stimulation protocols, which are usually not ablated.

In the context of the disclosed subject matter, "conduction" means the ability of a material to electrically conduct. This term is not synonymous with 'propagation of the activation wavefront'. Activation is the process of a cell depolarizing and in so doing affecting nearby cells to depolarize, starting an electrical chain reaction that spreads. Conduction is the transfer of charged molecules (ions) but this does not have to be through activation. Low level current can pass through cells which is not at the threshold for activation to occur.

Figure 9:
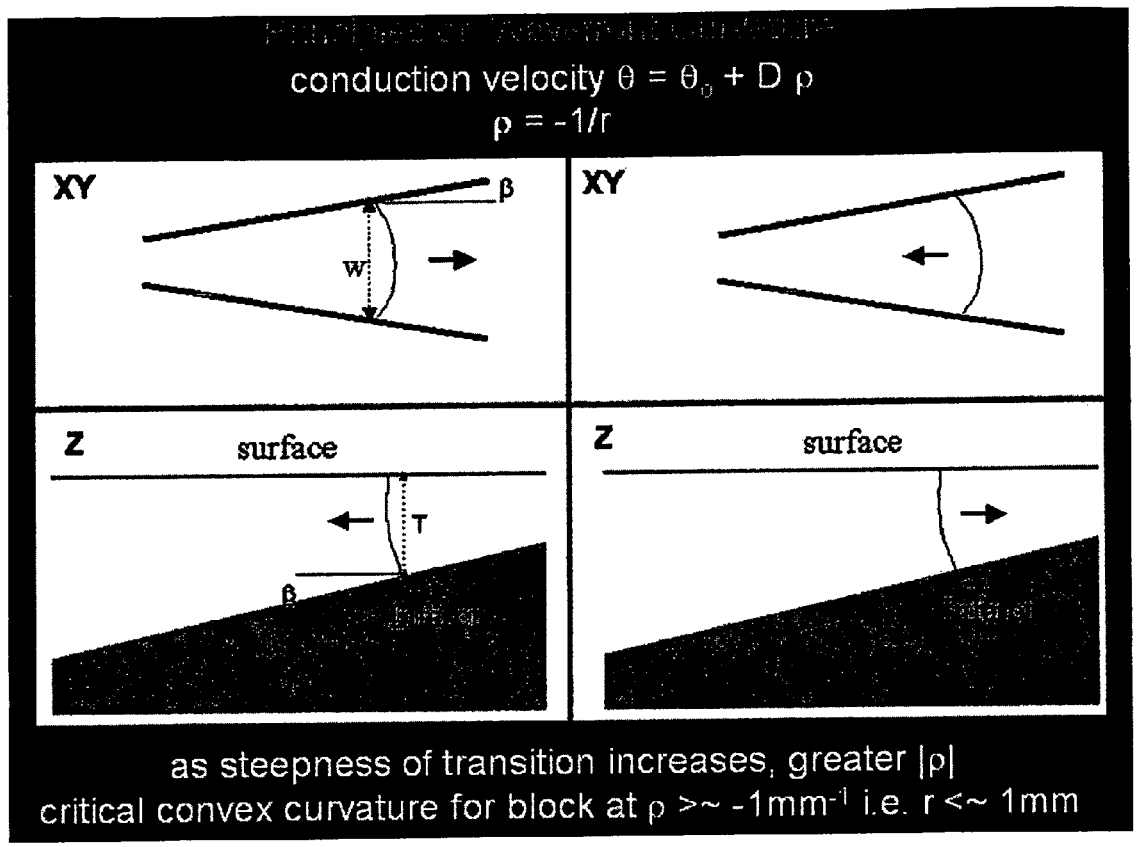
FIG. 9 shows how the curved wavefront looks when it goes toward an expanded or contracted area, along the surface plane (top) and in the tissue thickness direction (bottom) in accordance with an embodiment of the disclosed subject matter. The panels show that as the wavefront propagates toward a distal expansion it slows and potentially blocks. As the wavefront propagates toward a more constricted region its speed increases. Expansion or constriction of the wavefront occurs both in the XY plane (the surface plane of the heart) and/or along the Z axis (the direction in which the thickness of the border zone is measured). At the lateral borders of the wavefront, conduction cannot occur either because of functional or anatomical block.

In the context of the disclosed subject matter, "concave wavefronts" have faster than normal conduction velocity $\theta$ because rho ($\rho$) is positive (see Equation 4a and FIG. 9 right-hand panels). Convex wavefronts have slower than normal conduction velocity $\theta$ because rho ($\rho$) is negative (see Equation 4a and FIG. 9 left-hand panels).

In the context of the disclosed subject matter, "curvature" is the wavefront shape. It can be rectilinear (flat, planar, or straight line), convex (bending outward in the direction of travel), or concave (bending inward in the direction of travel).

In the context of the disclosed subject matter, an "electrophysiologic study" is the clinical investigation of the arrhythmia done by stimulating the patient's heart with electrical pulses using a catheter. The catheter is inserted into the patient's blood vessel and positioned in the heart using imaging technology (fluoroscopy). After ascertaining the best site to ablate, a lesion is created usually with radiofrequency energy (or other means such as laser or cryothermy).

In the context of the disclosed subject matter, "endocardial" is the interior surface of a heart chamber.

In the context of the disclosed subject matter, "epicardial" is the exterior surface of a heart chamber (or of the heart as a whole).

In the context of the disclosed subject matter, a "functional conduction block" is a conduction block that occurs due to the frequency of activation, i.e., the failure to recover excitability during the time interval of the cardiac cycle, or due to a second, intercepting activation wavefront which activates tissue ahead of the oncoming primary wavefront, causing the primary wavefront to block.

In the context of the disclosed subject matter, an "infarct" is an area of dead tissue that usually results when a coronary (heart) artery is blocked due to a clot or plaque, or other trauma to the heart tissue. The tissue dies because it does not receive blood with oxygen that it needs to live. This dead tissue does not conduct electricity and over time it is replaced with connective tissue, which also mostly does not conduct electricity. Thus the electrical activation wave must go around the region, and this often results in circular patterns of conduction, i.e., reentrant circuit loops.

In the context of the disclosed subject matter, a "myocardial infarct" ("MI") refers to the region of dead tissue in the myocardial (heart) tissue. The dead cells are gradually replaced with connective tissue during the period of months after MI. Connective tissue does not activate and mostly does not conduct the activation wave.

In the context of the disclosed subject matter, "cardiac fibrosis" involves increases in the collagen fiber content (de Bakker J M. Stein M. van Rijen H V, *Heart Rhythm*. 2(7):777-9, 2005). Both interstitial fibrosis (nonconducting fiber collects between myocardial cells) and/or the development of replacement fibrosis (fiber collects between bundles of cardiac muscle cells) are common types of cardiac fibrosis. Since the collagen fiber is nonconducting, it causes discontinuous conduction similar to that which occurs after myocardial infarction. Cardiac fibrosis can result in a zig-zag course of activation as well as impedance mismatch between current supply and current demand caused by a line of discontinuity between fibrotic and normal tissue. The larger structural barriers at the border zone of fibrotic regions with normal regions can result in functional conduction block due to the changes in wavefront curvature that occur at the discontinuities, thereby providing an anchor for stable reentrant ventricular tachycardia as in the case of myocardial infarction.

In the context of the disclosed subject matter, "heavily trabeculated myocardium" refers to spongy bone which is nonconducting and can occur at the atrial appendages and the right ventricular free wall of the heart (Coronel R., *Heart Rhythm* 2007; 4:1046-1047).

In the context of the disclosed subject matter, "structural remodeling" means a change in myocardial structure causing alterations in the geometry of viable tissue from normal. Said alterations can result in reentrant ventricular tachycardia if resulting changes in wavefront curvature are conducive to formation of arcs of conduction block at short cardiac cycle lengths.

In the context of the disclosed subject matter, a "border zone (BZ)" is the area of surviving tissue that still conducts electricity which is located between the infarct surface or the surface of other structurally remodeled heart tissue, and the heart surface. An infarct border zone (IBZ) is an example of a border zone.

In the context of the disclosed subject matter, an "isthmus" is the central common pathway, or common area, about which two or more loops of the reentrant circuit converge. The isthmus consists of an entrance point and an exit point for the activation wavefront as well as bounding arcs of conduction block. Because it is bounded (usually on two sides) by conduction block, it is called a "protected region". It is across the isthmus from one arc of conduction block to another that ideally an ablation lesion is placed to interrupt conduction along the circuit. Examples of the reentry isthmus with bounding arcs of conduction block are shown in FIGS. 4B, 5B, and 6B.

In the context of the disclosed subject matter, "lateral edges" are those edges of the isthmus at which the functional arcs of conduction block form during reentrant ventricular tachycardia. At these edges, there is a sharp change from thinnest to thick viable tissue in the direction radially outward from the isthmus.

In the context of the disclosed subject matter, the "left ventricle" is the heart chamber that pumps blood to peripheral organs. Within the wall of the left ventricle is usually the area where the infarct occurs.

In the context of the disclosed subject matter, "magnetic resonance imaging (MRI)" is a type of imaging technology that uses magnetism to generate images of the heart that can be obtained non-invasively and at high resolution. For imaging the heart, MRI it is often referred to as cardiac magnetic resonance. Using MRI, the infarct area, area of fibrosis or heavily trabeculated myocardium, or other structurally remodeled area can be identified by using a contrast agent such as gadolinium. This can be done in heart myocardial infarction (MI) patients and patients with cardiac fibrosis or other structural remodeling from which ventricular tachycardia can arise. Use of MRI in patients that have an implanted device, e.g. a defibrillator or pacemaker, may be problematic, depending on the composition of the implanted device. Currently the resolution is about 1 mm in patients and is continuously improving.

Any other imaging technology, such as, for example, ultrasound, that can image heart tissue at sufficient resolutions, can also be used in the methods of the disclosed subject matter to image the infarct area, area of fibrosis, or heavily trabeculated myocardium, or other structurally remodeled area.

In the context of the disclosed subject matter, a "normal zone" is the region where the myocardial tissue is normal. It conducts normally and has not been affected by the myocardial infarction. Because it is far from the infarcted area (the infarct is not embedded in the subsurface in the normal zone) it has normal thickness.

In the context of the disclosed subject matter, an "outer loop" or "outer pathway" is the part of the reentrant circuit loop that resides outside the isthmus.

In the context of the disclosed subject matter, "rectilinear wavefront" has normal conduction velocity θ (Equations 1-3) because rho (ρ) is zero (see Equation 4a).

In the context of the disclosed subject matter, a "reentrant circuit" means the pathway in which the activating wavefront propagates during reentry. This often occurs near the surface of the ventricle, e.g., often the endocardial surface, but sometimes at the epicardial surface.

In the context of the disclosed subject matter, "reentry" is the process of the activation wave reentering previously excited tissue by looping around through the same area.

In the context of the disclosed subject matter, "thickness" is the perpendicular distance from the infarct surface or other structurally remodeled surface to the heart surface through viable myocardial tissue (i.e., living tissue that conducts electricity and can electrically activate normally). At the border zone the viable tissue is thinnest. If its thickness is <~1 mm, functional conduction block can occur along any lateral edges where there is a sharp change to thicker tissue. These are areas where conduction block occurs during ventricular tachycardia around which the loops of the reentrant circuit occur.

In the context of the disclosed subject matter, "thickness" can also mean the straight line distance across the infarct surface or other structurally remodeled surface when this surface is three-dimensional (tubular) rather than two-dimensional (planar).

In the context of the disclosed subject matter, a "wavefront" is the leading edge of the activation wave.

As used herein, "storage device" is an electromagnetic apparatus, which has the capacity to store large numbers of signals permanently on magnetic or other media with the capability to retrieve the signals at any time.

As used herein, "processor" means an integrated circuit with the capability to process data based on collections of computer algorithms known as computer programs.

As used herein, "algorithm" means a set of arithmetic and logical statements used to process a set of numbers.

The disclosed subject matter provides a new geometric model describing the relationship between border zone (BZ), e.g., infarct border zone (IBZ) geometry and propagation of electrical activation wavefronts in reentrant circuits, which is then used to predict reentry isthmus location and candidate ablation sites.

Based on the model of the disclosed subject matter, areas of slow conduction and block during reentry coincide with regions where BZ thickness (T) is minimal and the thickness gradient (ΔT) is maximal, so that wavefront curvature ρ is maximized. Also based on the model, regions of fastest conduction velocity coincide with areas of minimum ΔT. Electrical and structural measurements were performed using canine postinfarction to illustrate an example of the model of the disclosed subject matter, which is described below.

To ascertain the model of the disclosed subject matter, which utilizes noninvasive imaging technology, BZ thickness resolution was 0.4 mm in MRI images and ~1 µm in histology imaging studies were performed as described in the Example below. Although these methods had different resolution, both are useful to distinguish areas where functional block would be expected to occur ($\rho > 1$ mm$^{-1}$), as compared with slow conduction regions when present at the entrance and exit to the isthmus (0 mm$^{-1} < \rho < 1$ mm$^{-1}$) and rapid conduction regions elsewhere in the circuit ($\rho \sim 0$ mm$^{-1}$).

Thus, in one embodiment, it is shown that imaging of the heart, e.g. with MRI, which has high resolution, is useful to extract the geometric structure of the conducting medium for correlation with activation pattern characteristics. In addition, this provides an advantage over other methods for ascertaining geometric structure of the heart because it is noninvasive. The geometric model that is described herein is therefore also useful, for example, to predict how the evolution of the structural properties of the tissue will affect reentry inducibility. For example, the period of arrhythmogenesis in canine postinfarction is not precisely known. However, replacement of infarcted tissue with connective tissue occurs over time. The rate and character of structural changes will likely determine reentry inducibility as predicted by the model. Similarly, the rate and character of fibrosis, trebeculation, or other structural changes causing structural remodeling of heart tissues will likely determine reentry inducibility as predicted by the model.

Imaging, such as cardiac magnetic resonance imaging, is a useful tool for analysis of postinfarction ventricular tachycardia and other structural remodeling in clinical patients. In human postinfarction, BZ geometric properties are more permanent than in canine postinfarction, and arrhythmogenicity often continues so long as the patient remains untreated. Thus, in one embodiment, the disclosed subject matter includes methods for applying the BZ geometry model for prediction of reentrant ventricular tachycardia and its characteristics in postinfarction patients or patients with other structural remodeling of heart tissues.

Figure 11:
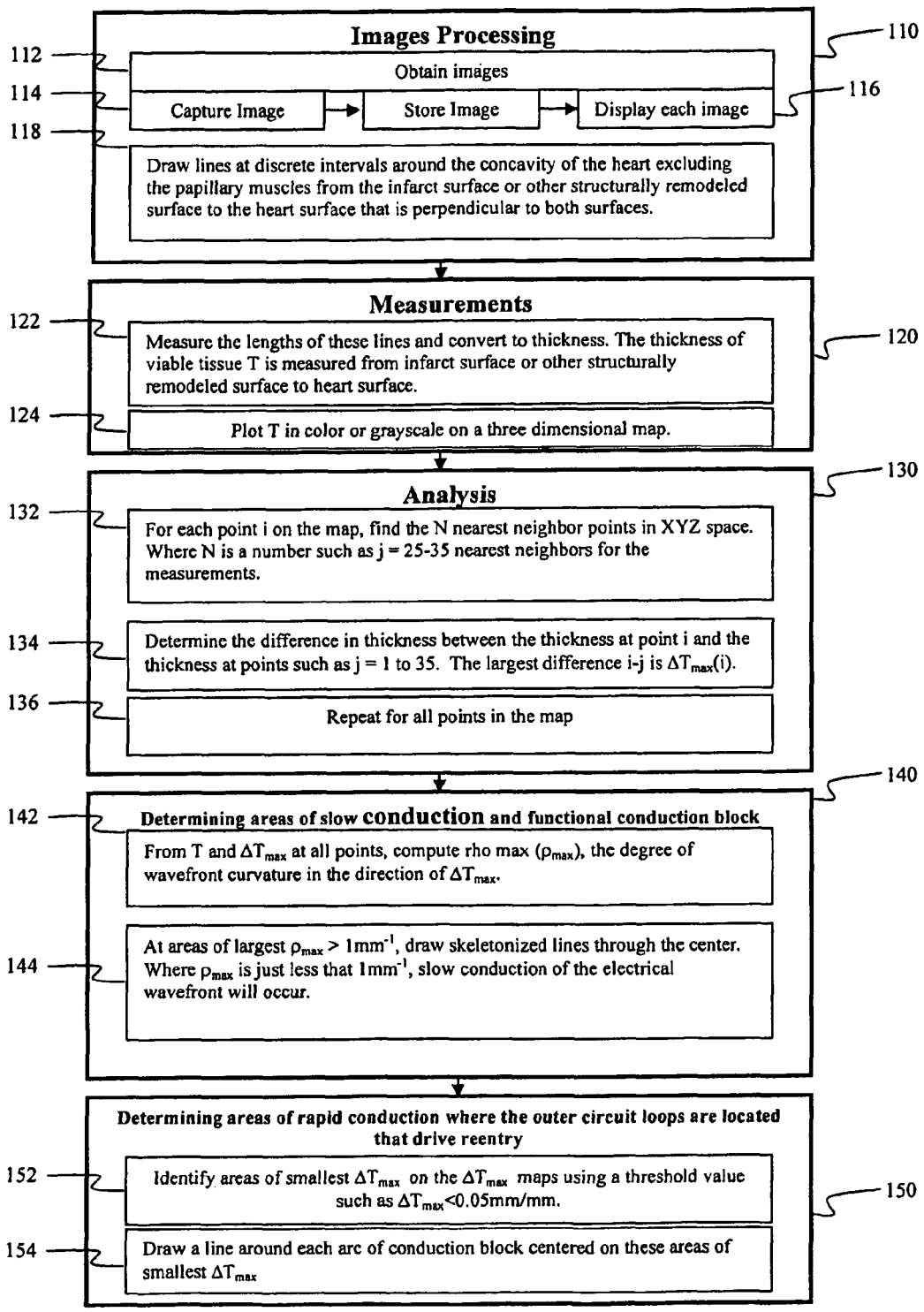
FIG. 11 is a chart illustrating the system of identifying the location of a candidate ablation site in accordance with an embodiment of the disclosed subject matter.
Figure 12:
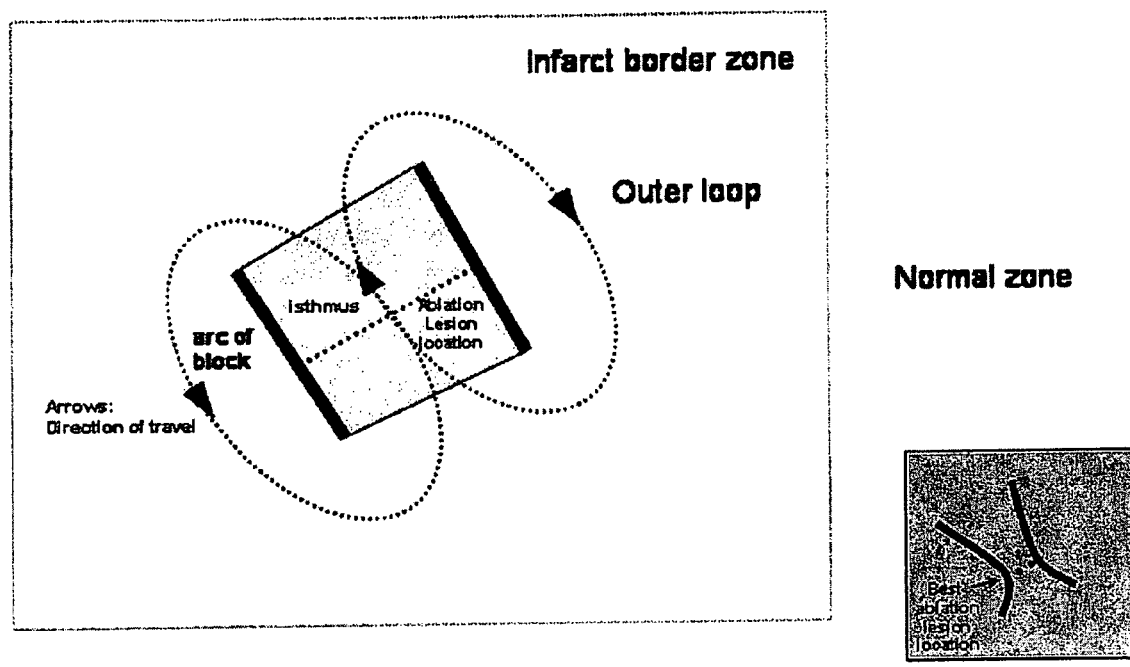
FIG. 12 is a schematized version of a reentrant circuit showing the electrical activation characteristics. The reentry isthmus, or central common pathway, is shown with medium gray shading at the center of the figure. It is bounded along its lateral edges by arcs of conduction block (thick black lines). The electrical activation wave propagates through the isthmus from bottom right to top left in the figure as denoted by the central arrow. Near the exit, the wavefront bifurcates into two distinct electrical waves which turn right and left. Each wave propagates around the arcs of conduction block in areas known as the outer loops of the reentrant circuit. When these distinct waves arrive near the entrance of the isthmus they coalesce again forming a single wavefront. This process occurs once each cardiac cycle. Propagation of the activation wavefront is only constrained within the confines of the isthmus. If an ablation lesion were to be placed across the isthmus from one lateral edge to the other, it would block electrical conduction and thus prevent reentry from occurring to thereby provide therapy for patients with ventricular tachycardia that is caused by a reentrant circuit. The lateral edges of the isthmus are not always uniform and parallel to each other as in the central figure. They may be curvy, so that there is a distinct narrowed portion at some location along the isthmus. In that case, the narrowed area would be the best site to place an ablation lesion to minimize its length across the isthmus (see inset).
Figure 13:
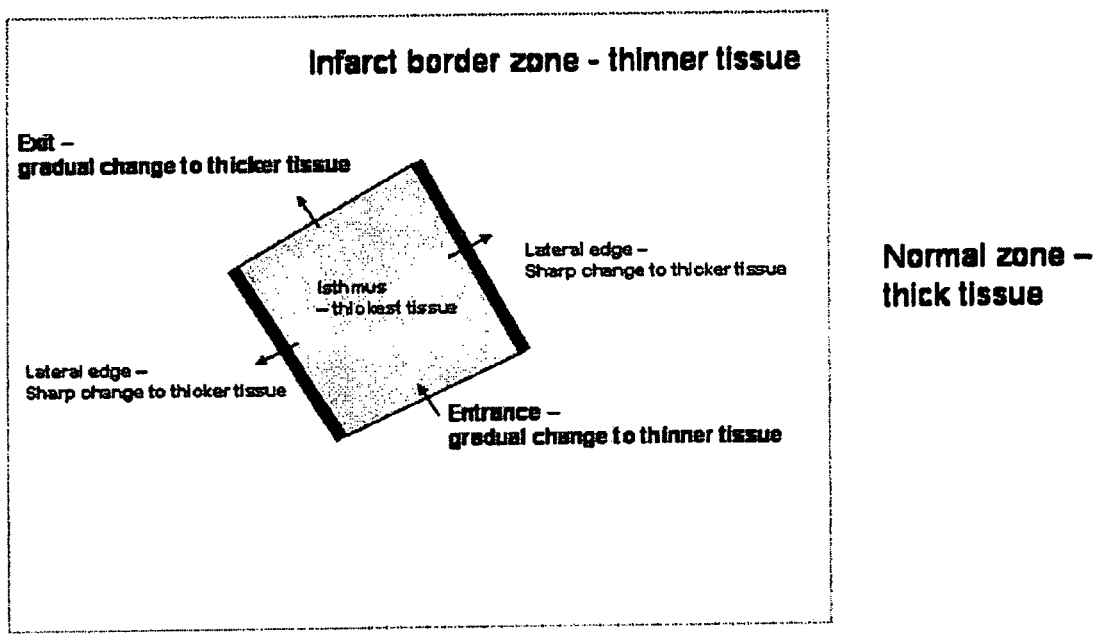
FIG. 13 illustrates the geometric relationships of the viable substrate to the features of the reentrant circuit. The border zone is a layer of surviving myocardium superficial to an infarcted region of the heart in patients who have had a myocardial infarction or MI. The normal zone is an area of tissue away from the infarcted regions in these patients that is not located superficial to the infarct region, where "superficial" means closer to the surface of the heart. As in FIG. 12, the isthmus is shown as a medium gray region which is bounded at the lateral edges by arcs of conduction block (thick black lines). Due to the relationship between the geometry of the viable tissue and wavefront curvature, at the short cardiac cycle lengths that occur during ventricular tachycardia, the wavefront cannot propagate radially outward across the lateral edges, thus conduction block occurs there. This is due to the fact that the tissue has a large electrical impedance mismatch across these edges caused by the approximately step change from thinnest to thicker viable myocardial tissue at this area of the border zone. However, at the entrance and exit points to the isthmus which are denoted by arrows, there is a more gradual change in thickness, reducing the electrical impedance mismatch and thereby allowing the activation wavefront to propagate through both the entrance and exits, so long as the steepness of the incline change in the thickness of the viable tissue is not too great. These relationships are described by Equations 4-9.

In still another embodiment, the disclosed subject matter provides an algorithm identifying the location of a candidate ablation site in a patient, e.g., a myocardial infarct patient, which may be carried out using a processor. In some embodiments, the system includes the following (see the chart of FIG. 11). Images, such as MRI images, are captured and stored (112, 114). In one embodiment, each image is displayed on a processor (116). For each image, a line is drawn from the infarct or other structurally remodeled surface to the heart surface that is perpendicular to both surfaces (118). In one embodiment, this is done at discrete intervals around the concavity of the heart excluding the papillary muscles (see FIG. 1E). The papillary muscles are excluded by the gray line. The lengths of these lines are measured and converted to thickness. Thus, in one embodiment, the thickness of viable tissue T is measured from infarct surface or other structurally remodeled surface to heart surface (122).

In a further embodiment, T is plotted in color or grayscale on a three dimensional map (124). In a related embodiment, the XY plane can denote the position in the image and the Z axis corresponds to the image slide number. XYZ are Cartesian coordinates. Each point on the map thus can provide the thickness (T) of viable tissue and its XYZ location on the heart. Exemplary maps of thickness (T) are shown in FIGS. 1D and 1F, FIGS. 4C, and 5C-D, 6C-D, 7C-D.

For analysis of the data (130), in one embodiment, for each point (i) on the map, the N nearest neighbor points in XYZ space are identified (132). In one embodiment, N is a number which can be set at, for example, j=25-35 nearest neighbors for the measurements.

In one embodiment, the difference in thickness between the thickness at point i and the thickness at points, for example, j=1 to 35 is determined. Whatever difference i-j is largest, is denoted as $\Delta T_{max}(i)$ (134). In another embodiment, this is repeated for all points in the map (136). In still another embodiment, a new three dimensional map, of $\Delta T_{max}(i)$ can be created from these values. This is described in FIGS. 3B and 3C. Maps of $\Delta T_{max}$ are shown in FIGS. 4D, and 5E-F, 6E-F, 7E-F, for example.

In another embodiment, in order to determine areas of slow conduction and functional conduction block (140), rho max ($\rho_{max}$), the degree of wavefront curvature in the direction of $\Delta T_{max}$, is computed from T and $\Delta T_{max}$ at all points (142). For example, Equation 9 is used for this purpose. Since rho is known for all points, a map of $\rho_{max}$ can then be created. Exemplary maps of $\rho_{max}$ are shown in FIGS. 4E, and 5G-H, 6G-H, 7G-H.

In one embodiment, at areas of largest $\rho_{max} > 1$ mm$^{-1}$, skeletonized lines can be drawn through the center. These are the estimated positions of actual conduction block during reentrant ventricular tachycardia. They are shown as gray lines in FIGS. 4E, and 5G, 6G, and 7G, for example. The actual lines of block are overlaid as black lines in FIGS. 4E, and 5G, 6G, and 7G.

The actual lines of block are determined by activation mapping. Activation maps of the arrhythmia, ventricular tachycardia, are shown in FIGS. 4B, 5B, 6B, and 7B, for example.

In one embodiment, where $\rho_{max}$ is just less that 1 mm$^{-1}$, slow conduction of the electrical wavefront will occur (144).

In another embodiment, to determine areas of rapid conduction where the outer circuit loops are located that drive reentry (150), areas of smallest $\Delta T_{max}$ on the $\Delta T_{max}$ maps are identified using, for example, a threshold value such as $\Delta T_{max} < 0.05$ mm/mm (152). A line is drawn around each arc of conduction block centered on these areas of smallest $\Delta T_{max}$ (154). This will be the route of fastest conduction and therefore the center of the driving route around each loop of the circuit.

The present disclosure is further illustrated by the following example, which should not be construed as further limiting.

EXAMPLE

A New Geometric Model Describing the Relationship Between Border Zone (BZ) Geometry and Wavefront Propagation in Reentrant Circuits in a Canine Model Methods In seven mongrel canines weighing 20-40 kg, the LAD coronary artery was ligated near its base while under sodium pentobarbital anesthesia (30 mg/kg IV) (Dillon S M, et al., *Circ Res* 1988; 63:182-206). The resulting infarction in the anterior left ventricle resulted in an BZ which extended to the epicardium. The animals were prepared for electrophysiologic analysis 3-5 days after LAD ligation, and programmed electrical stimulation was used to induce tachycardia. Electrograms from the epicardial surface of the BZ were recorded using a multichannel bipolar array and data acquisition system, and activation maps of sinus rhythm and ventricular tachycardia were then constructed.

From reentrant ventricular tachycardia maps, the isthmus border was defined as the location of bounding functional lines of block that were connected by straight lines at their ends (Ciaccio E J, et al., *J Cardiovascular Electrophysiol* 2004; 15:27-36; Ciaccio E J, et al., *Circulation* 2001; 104:613-619). The outer pathway was defined as the reentrant circuit location outside the isthmus where it still overlapped the infarct. Following electrophysiologic analysis, the heart was excised and prepared for thickness measurement using either histologic analysis (n=4 canine postinfarction experiments) or Magnetic Resonance Imaging (MRI) analysis (n=3 experiments). In this series of experiments, measurement of border zone thickness using histologic analysis was used to validate measurement of border zone thickness done with magnetic resonance imaging.

Thickness Measurements

Thickness measurements (1 μm resolution) were made from histology images using computer software (Spot Diagnostic Instruments, Sterling Heights, Mich.). An arrow was projected at right angles from the connective tissue layer at the epicardial surface to the necrotic region of infarcted tissue at depth (FIGS. 1A-B). The arrow length (BZ thickness T) was calculated automatically, and the isthmus region tended to be thinner than the outer pathway (FIGS. 1A-B).

The tissue samples for histology thickness measurements were taken at 5 mm intervals over a 5×5 cm area of the BZ (100 total slides). Six thickness measurements were made at random locations on each slide and averaged. A BZ thickness map was constructed after interpolating and smoothing the XY coordinates to a final resolution of 0.4×0.4 mm in the surface plane (FIG. 1C). Thickness measurements with 1 μm resolution were made from MRI images using ImageJ (National Institutes of Health, Bethesda, Md.). Each MRI slice had a pixel resolution of 0.4×0.4 mm and the distance between slices was 0.4 mm. A representative slice is shown with thickness measurement lines denoted in black (FIG. 1E; view is from base to apex).

Measurement lines were spaced ~2 mm apart by hand and extended from the connective tissue layer to the contiguous infarct (yellow-white in FIG. 1E), or to the concavity of the endocardial surface excluding the papillary muscles (denoted in part by gray line). The line length (BZ thickness T) and its position in Cartesian coordinates were automatically computed by ImageJ.

From all sample points, a three-dimensional LV thickness map was constructed using map3d (MacLeod R S, Johnson C R. Map3d: Interactive Scientific Visualization for Bioengineering Data. IEEE Engineering Medicine Biology Society 15th Annual International Conference, pp 30-31, 19) (FIGS. 1D,F). The approximate slice location of panel E is denoted by the black dashed lines in panels D and F. Correspondence between the MRI map (panel E) and thickness maps (panels D-F) are shown at selected locations by different circles. The thinnest point in the BZ is ~50 μm and it overlaps the infarct (FIGS. 1D-E). Thickest LV regions are ~9.5 mm (dark gray, FIGS. 1D,F).

Geometry-to-Propagation Model: Relationships that Provide a Basis for Equations

In the context of the disclosed subject matter, this section presents a geometry-to-propagation model and explains relationships that provide a basis for equations provided below.

Figure 2:
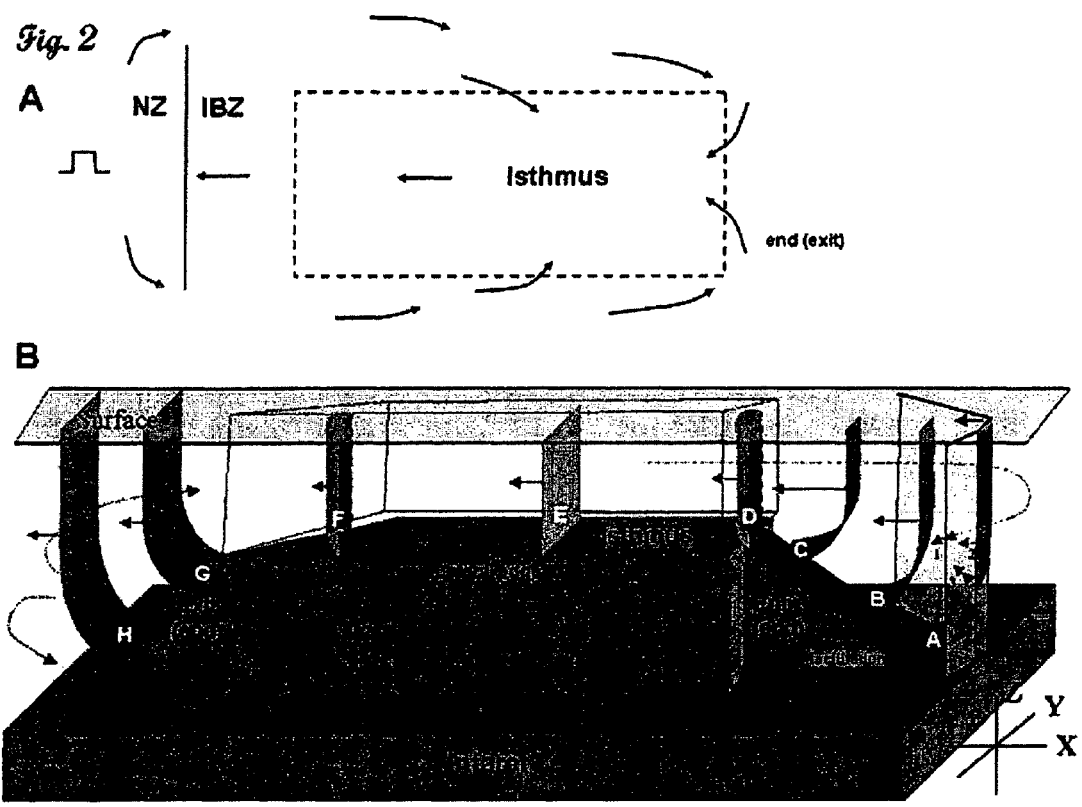
FIG. 2. illustrates characteristics of reentrant ventricular tachycardia.

During reentrant ventricular tachycardia, the activation wavefront curvature is related to BZ geometry as depicted in FIG. 2. A diagram of wavefront propagation during the extrastimulation cycle is shown in FIG. 2A. The stimulus location is at left and arrows denote the direction of activation. When stimulating from outside the BZ, the premature stimulus, depending on the S1-S2 coupling interval, blocks within the border zone near its boundary with the normal zone (BZ: mean refractory period of ~199 ms, NZ: mean refractory period ~159 ms) (Cabo C, Boyden P. et al., *Am J Physiol Heart Circ Physiol* 2003; 284:H372-H384). The wavefront then bifurcates and gradually activates the entire BZ including the region where the isthmus will form, turning in the opposite direction and eventually breaking through the unidirectional block line to initiate reentry.

In FIG. 2B, three-dimensional wavefront curvature is depicted during a reentry cycle. The infarct is shown at the bottom and the epicardial surface as a clear sheet at top. As previously described, (Peters N S, et al., *Circulation* 1997; 95:988-996) a rectangular plateau of thinnest BZ coincides with the reentry isthmus. At the plateau's lateral boundaries, step changes in infarct depth correspond with functional block line locations, whereas at the plateau's ends, gradual thickness change (ramps) coincide with entrance and exit points to the isthmus. The expected three-dimensional wavefront curvature at various locations during reentry is denoted by surfaces that are concave (A, B, and C), rectilinear or flat (E), or convex (F, G, and H), and propagation direction during a reentry cycle is denoted by arrows.

Near the isthmus entrance, the wavefront is concave (Kogan B Y, et al., *Physica D* 1992; 59:275-296; Cabo C, et al., *Circ Res* 1994; 75:1014-1028; Kleber A G, Rudy Y. *Physiol Rev* 2004; 84:431-488) in the XY plane due to convergence of the two bifurcated portions of the double-loop wavefront (denoted as transparent sheets labeled 1-3). Concave curvature also occurs along the thickness axis (Z-axis) due to diminishing BZ thickness during propagation toward the plateau (wavefronts A-C). Since concave curvature causes the wavefront to accelerate (Kogan B Y, et al., *Physica D* 1992; 59:275-296; Cabo C, et al., *Circ Res* 1994; 75:1014-1028; Kleber A G, Rudy Y. *Physiol Rev* 2004; 84:431-488), conduction is facilitated toward the isthmus perimeter, which is therefore the fastest direction for propagation. At the isthmus entrance, the wavefront proceeds through a narrowed aperture where it is constrained by the bounding functional arcs of block, and then it suddenly becomes convex in the XY plane at the distal expansion into the isthmus (point D).

Since convex curvature causes the wavefront to decelerate, propagation is slowed at point D and there is the potential for block. The wavefront does not block at this expansion so long as the safety factor remains above unity, which is in part facilitated by the extra current available within one space constant preceding the aperture (Kleber A G, Rudy Y., *Physiol Rev* 2004; 84:431-488; Ramza B M, et al., *Circulation Research* 1990; 66:147-162). Hence, entrance to the isthmus is more likely to succeed when wavefront curvature is concave toward the entrance point and the incidence angle is 90°, which will occur when there is a gradual decrease in BZ thickness in that direction, as shown.

Within the isthmus, if infarct depth and the distance to the lateral walls in the XY plane is level, then the wavefront becomes flat (E). At the isthmus exit, the wavefront becomes convex along the XY plane at the distal expansion away from the block lines (F), and along the Z-axis due to increasing BZ thickness following the exit point (G-H). When thickness increases more gradually away from the exit, Z-axis convexity is reduced, increasing the safety factor so that the wavefront is more likely to propagate. Hence, successful propagation out of the isthmus would be expected to occur at an edge of the plateau having a relatively gradual thickness increase in the radially outward direction (as at the actual exit point in FIG. 2B).

About the lateral isthmus edges where there is a step change in thickness, functional block would be expected to occur due to the large wavefront convexity along the Z-axis as it propagates radially outward at those locations. In the case of approximately symmetric geometry about the isthmus (FIG. 2B), either end can potentially act as an entrance or exit depending on the extrastimulation point, i.e., two opposite reentrant circuit morphologies would be possible (Ciaccio E J, et al., *J Cardiovasc Electrophysiol.* 2004; 15:1293-1301; Ciaccio E J. *J Cardiovascular Electrophysiology* 2005; 16:646-654; Costeas C, et al., *Circulation.* 1997; 96:3721-3731).

Geometry-to-Propagation: Model Equations

A set of equations was developed relating BZ geometry to excitation wavefront propagation. The velocity of impulse conduction without curvature $\theta_o$ is dependent upon the longitudinal resistance R of the conducting medium (Kleber A G, Rudy Y. *Physiol Rev* 2004; 84:431-488):

$$\theta_o^2 \propto 1/R \quad (1)$$

The overall conduction velocity is:

$$\theta = \theta_o + \theta_c \quad (2)$$

where the conduction velocity contribution $\theta_c$ is due to wavefront curvature. In the border zone, $\theta_c$ can be estimated as follows:

$$\theta_c = D\rho \quad (3)$$

where D is the diffusion coefficient (the current flow due to the transmembrane potential gradient, with value of 0.05-0.2 mm$^2$/ms in ventricular myocardium Clayton R H, Holden A V., *Physiol Meas* 2002; 23:707-726) and $\rho$ is the degree of wavefront curvature in mm$^{-1}$.

Thus:

$$\theta = \theta_o + D\rho \quad (4a)$$

and since $\rho = -1/r$ $$\theta = \theta_o - D/r \quad (4b)$$

where r is the local radius of curvature. As the steepness of transition increases (FIG. 9), convex curvature which occurs as the wavefront propagates toward a distal expansion increases, causing wavefront slowing, and leading to conduction block when $\rho > \sim -1$ mm$^{-1}$ i.e., $r < \sim 1$ mm.

Figure 3:
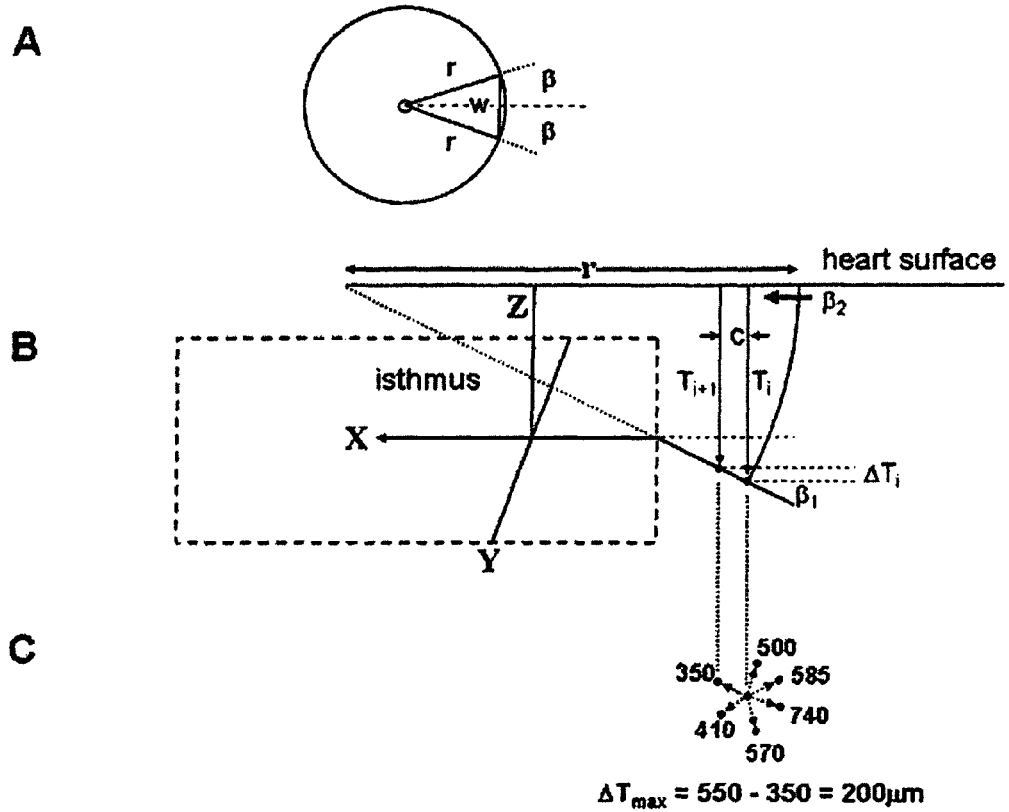
FIG. 3 illustrates the mathematical relationships used to formulate the geometric model, in accordance with an embodiment of the disclosed subject matter.

As a first approximation, suppose that no-flux conditions exist at lateral borders (Kogan B Y, et al., *Physica D* 1992; 59:275-296; Sampson K J, Henriquez C S., *Chaos* 2002; 12:819-828), so that the wavefront edges must be perpendicular to the boundary points. When propagating through constrained regions with no-flux boundaries, wavefront curvature can be modeled as a circular arc (Kogan B Y, et al., *Physica D* 1992; 59:275-296). As depicted in FIG. 3A:

$$r = (w/2)/\sin(\beta) \quad (5)$$

where r is the radius of the circle forming the wavefront shape, w is the chord width, and $\beta$ is the angle from the midline to the lateral borders.

For canine postinfarction, the BZ is bounded along the Z-axis (thickness axis) by the infarct at depth and by the epicardial surface of the heart. If the wavefront propagates in parallel with the surface, then β is a constant 90° in that direction but will vary in the infarct direction. FIG. 3B shows the geometric principles. Suppose the activation wavefront is propagating up an incline (spatial decrease in BZ thickness) toward the isthmus entrance as from point i to i+1. BZ thickness changes from $T_i$ to $T_{i+1}$ as shown. The change in thickness is $\Delta T_i$, the space step from i to i+1 is a distance c, the angle with the infarct surface in the direction of propagation is $\beta_1$ and with the heart surface it is $\beta_2$=90°. At each space step, curvature in the XZ plane is calculated.

Using trigonometry it can be estimated:

$$\sin(\beta) = \Delta T/(c^2 + \Delta T^2)^{1/2} \quad (6)$$

Substituting Equations 5-6 into 4b:

$$\theta = \theta_o - D \cdot \Delta T/[T \cdot (c^2 + \Delta T^2)^{1/2}] \quad (7)$$

where w/2=T (FIGS. 3A-B). Thus:

$$\rho = -\Delta T/[T \cdot (c^2 + \Delta T^2)^{1/2}] \quad (8)$$

Let $\Delta T_{max}$ at a particular node (x, y) be the largest absolute magnitude change in thickness in the vector field about a local region in any direction (x+Δx, y+Δy). In FIG. 3C, hypothetical thickness values in microns are shown surrounding node i. Let $T_i$=550 μm. The surrounding thickness values with greatest difference from $T_i$, 350 and 740 μm, are oriented approximately in the direction of greatest incline in FIG. 3B. Based on these hypothetical values at node i, $\Delta T_{max}$=550−350=200 μm. From the $\Delta T_{max}$ calculated at any particular node, the maximum possible degree of wavefront curvature in the vector field about that node is:

$$\rho_{max} = \Delta T_{max}(x, y)/[T(x, y) \cdot (c^2 + \Delta T_{max}(x, y)^2)^{1/2}] \quad (9)$$

which occurs when the wavefront propagates across the node in the direction of largest ΔT. At any BZ areas where the spatial change in thickness is relatively small ($\Delta T_{max} \ll c$):

$$\rho_{max} \approx \Delta T_{max}/(c \cdot T) \quad (10)$$

In ventricular myocardium, it has been shown experimentally and by computer model (Cabo C, et al., *Circ Res* 1994; 75:1014-1028; Fast V G, Kléber A G. *Cardiovascular Research* 1997; 33:258-271) that functional conduction block occurs at a typical ventricular tachycardia cycle length in canine postinfarction (175-225 ms) when r~1 mm. Therefore, it can be anticipated that an absolute value of $\rho_{max} \gtrsim 1$ mm$^{-1}$, as estimated by Equations 9-10, would be indicative of very slow conduction or block during reentrant tachycardia when the wavefront propagates from the thinner isthmus region radially outward to areas of thicker viable tissue (convex wavefront curvature).

To predict regions with most rapid conduction velocity in the BZ during reentrant tachycardia, suppose that the total change in thickness Z from isthmus to outer pathway or vice versa occurs at a single space step j:

$$dT_i = Z,$$

where i=j $$dT_i = 0,$$

where i≠j

In the direction from thinner to thicker tissue (isthmus to outer pathway), very slow conduction or block will occur at j if Z is sufficiently large, due to the large convex wavefront curvature at the step change in tissue thickness (large impedance mismatch). In the direction from thicker to thinner tissue (outer pathway to isthmus), a transient increase in θ will occur at space step j due to the concave wavefront curvature, but $\theta = \theta_o$ elsewhere along the path. It can be postulated that in either direction, gradual rather than step changes in T will minimize the transit time TT over n space steps. TT can be estimated by substituting Equation 10, useful when ΔT is of low magnitude along the path of propagation, into Equation 4a with ρ estimated as $\rho_{max}$, and then inverting and writing as a differential:

$$TT = \sum \{1/[\theta_o - D(dT_i/c \cdot T_i)]\} \quad (11)$$
$$= \sum \{T_i/[\theta_o T_i - (D/c)dT_i]\}$$

for i=1 to n space steps. Since $T_{i+1} = T_i + dT_i$, and $dT_i$ is the thickness change between space steps i and i+1:

$$TT = \sum \{T_i/[\theta_o T_i - (D/c)T_{i+1} + (D/c)T_i]\} \quad (12)$$
$$= \sum \{T_i/[(\theta_o + (D/c))T_i - (D/c)T_{i+1}]\}$$

Let $c_1 = \theta_o + (D/c)$, $c_2 = D/c$, and let v represent the denominator. To minimize TT from thin tissue (isthmus location) to thick tissue (outer pathway) or vice versa, the quotient rule is used and the equation set to zero:

$$0 = \Sigma\{[c_1 T_i dT_i - c_2 T_i dT_{i+1}] - [c_1 T_i dT_i - c_2 T_{i+1} dT_i]\}/v^2$$

$$0 = \Sigma\{c_2(T_i dT_{i+1} - T_{i+1} dT_i)\}/v^2 \quad (13)$$

Figure 10:
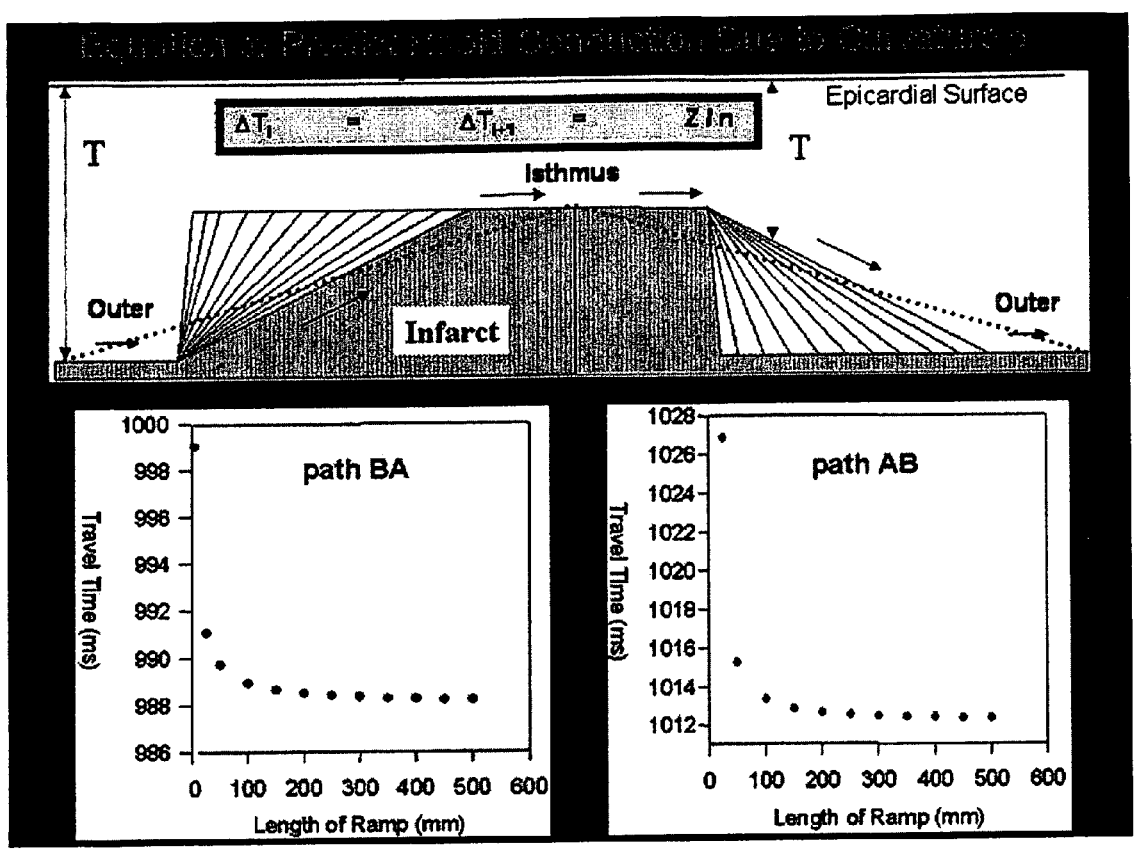
FIG. 10 shows the relationship between travel time and the ramp change in tissue thickness that the electrical wavefront travels over in accordance with an embodiment of the disclosed subject matter. The panels show that the optimal change in border zone thickness for fastest travel time occurs when the ramp is uniform ($\Delta T$=constant) from isthmus to outer circuit pathway or vice versa. When sharper ramp changes in thickness occur over shorter distances, the travel time is increased. This is also illustrated by the scatterplots below the illustrations. Based on the wavefront curvature Equations 10-15, the travel time from isthmus to outer circuit pathway or vice versa is longest when the change in thickness between these two regions occurs all at once (step function). As there is a more gradual change, the travel time diminishes. The outer reentrant circuit loop takes the path of least resistance, i.e., it propagates in the direction to minimize the travel time, which is determined in this system by maps of thickness gradient $\Delta T$.

Thus:

$$\Sigma(T_i dT_{i+1})/v^2 = \Sigma(T_{i+1} dT_i)/v^2 \quad (14)$$

which has an approximate solution of:

$$dT_i = dT_{i+1} = Z/n,$$

i=0, n−1 (15)

for n space steps and a total thickness change Z from isthmus to outer pathway or vice versa, regardless of whether the sign of $dT_i$ is positive or negative (wavefront convex or concave). Thus, according to Equation 15 (FIG. 10), a constant, minimized thickness change ΔT along the path would be expected to minimize TT and therefore maximize θ whether traveling from the isthmus to outer pathway or vice versa.

Measurements and Statistics $\Delta T_{max}$ was computed (see FIG. 3C) from N=25 surrounding points to calculate, from Equation 9, $\rho_{max}$ at all grid nodes. From maps of these values, estimated block lines were drawn in the center of distinct regions having $\rho_{max} > 1$ mm$^{-1}$. The estimated line locations were compared with actual block line locations determined from tachycardia activation mapping by averaging the distance between five equally spaced corresponding points on each line. A straight line was drawn midway between estimated block lines on the grid and calculated the percentage of actual isthmus width that would be blocked if this line was used as an estimated ablation line. Areas of fastest conduction velocity about the reentrant circuit were estimated, according to the result given in Equation 15, to be contiguous regions with minimum $\Delta T_{max}$.

A threshold selected $\Delta T_{max} < 0.05$ mm/mm, i.e., <25% of the largest expected $\Delta T_{max}$ of 0.2 mm/mm in close proximity to the isthmus that was observed previously (Peters N S, et al.,

*Circulation* 1997; 95:988-996). Actual reentrant ventricular tachycardia conduction velocity was measured at 5 random points on the activation map in the region with minimum $\Delta T_{max}$, at 5 random points at entrance-exit areas, and from 5 random points throughout the outer pathway and averaged over each of these three regions. Conduction velocity was measured as the difference in activation time between a pair of adjacent recording sites divided by the distance between them. The sites were selected such that the vector orientation overlapping their locations was in parallel with the direction of wavefront propagation.

The unpaired t-test and one-way ANOVA were used to determine the statistical significance of the difference in means between variables ($p<0.05$). The sensitivity of the geometric model for detecting isthmus location was calculated as the area of the actual isthmus that was overlapped by the estimated isthmus, divided by the area of the actual isthmus. The specificity was calculated as the area of the border zone that was not overlapped by the actual or estimated isthmus, divided by the area of the border zone that was not overlapped by the actual isthmus. Because the entire extent of the BZ in histology experiments was not measured, a constant 5×5 cm area was used as the approximate area of the border zone for all specificity calculations. Measurements of area (actual area from activation and estimated area from $\rho_{max}$) and their overlap were determined from the computerized maps using ImageJ.

Results

Consequently, of seven canine postinfarction experiments, four had only inducible sustained reentrant ventricular tachycardia with a mappable circuit (single morphologies), two had only inducible nonsustained reentrant ventricular tachycardia with a mappable circuit (single morphologies), and one had inducible tachycardia but no mappable reentrant circuit.

Figure 4:
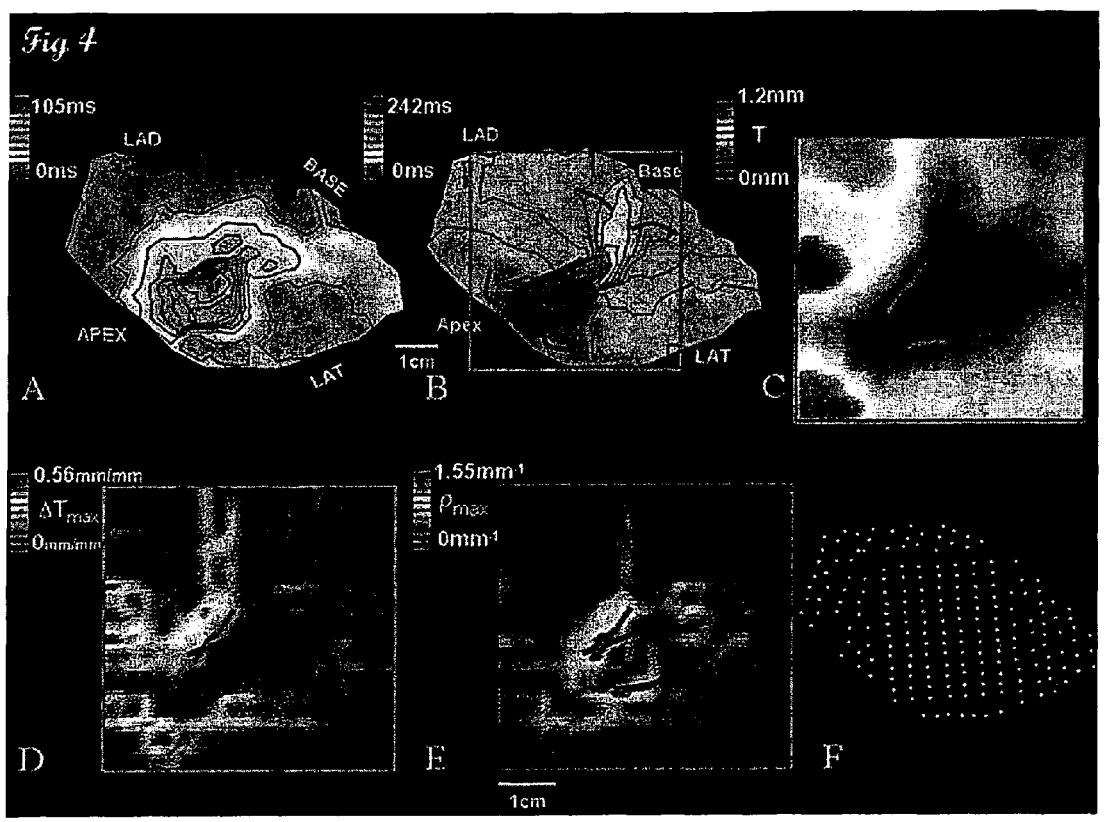
FIG. 4 represents BZ maps for a selected postinfarction canine experiment in accordance with an embodiment of the disclosed subject matter.

An example of activation mapping and analysis of infarct depth after histologic measurement is given in FIG. 4. The panels show activation maps of sinus rhythm (FIG. 4A), tachycardia (FIG. 4B), thickness map T (FIG. 4C), maximum gradient $\Delta T_{max}$ (FIG. 4D), maximum curvature $\rho_{max}$ estimated from Equation 9 (FIG. 4E), and the bipolar electrode grid configuration (FIG. 4F). Colors from white-to-gray denote early-to-late activation with isochrones spaced 10-20 ms apart (FIGS. 4A-B), larger-to-smaller thickness T (FIG. 4C), and greater-to-lesser $\Delta T_{max}$ and $\rho_{max}$ (FIGS. 4D-E).

In the tachycardia activation map (FIG. 4B), conduction block is denoted by thick curved black lines, wavefront propagation direction is given by arrows, and the thickness measurement area is delineated by the square. Tachycardia is caused by a double-loop reentrant circuit (FIG. 4B, arrows) with slow sinus rhythm activation at the isthmus region (FIG. 4A). The BZ is thinnest at the approximate isthmus location (FIG. 4C), and relatively steep thickness changes $\Delta T_{max}$ occur near the lateral boundaries (FIG. 4D). Estimated functional block line locations were derived from the map of FIG. 4E and are centered at areas of greatest $\rho_{max}$ (gray lines); actual block line locations are overlaid on the map (black lines).

Actual and estimated line locations were then also overlapped on panels C and D. The estimated and actual arcs of block do not precisely coincide (also in FIG. 5) which is likely due in part to slight measurement error and distortion during the projection process. Not all areas of large $\Delta T_{max}$ (FIG. 4D) are manifested as areas with large $\rho_{max}$ (FIG. 4E) because $\rho_{max}$ is also proportional to 1/T (Equations 9-10). Thus where thickness T is large (light gray and white in FIG. 4C), $\rho_{max}$ tends to be small (FIG. 4E).

Figure 5:
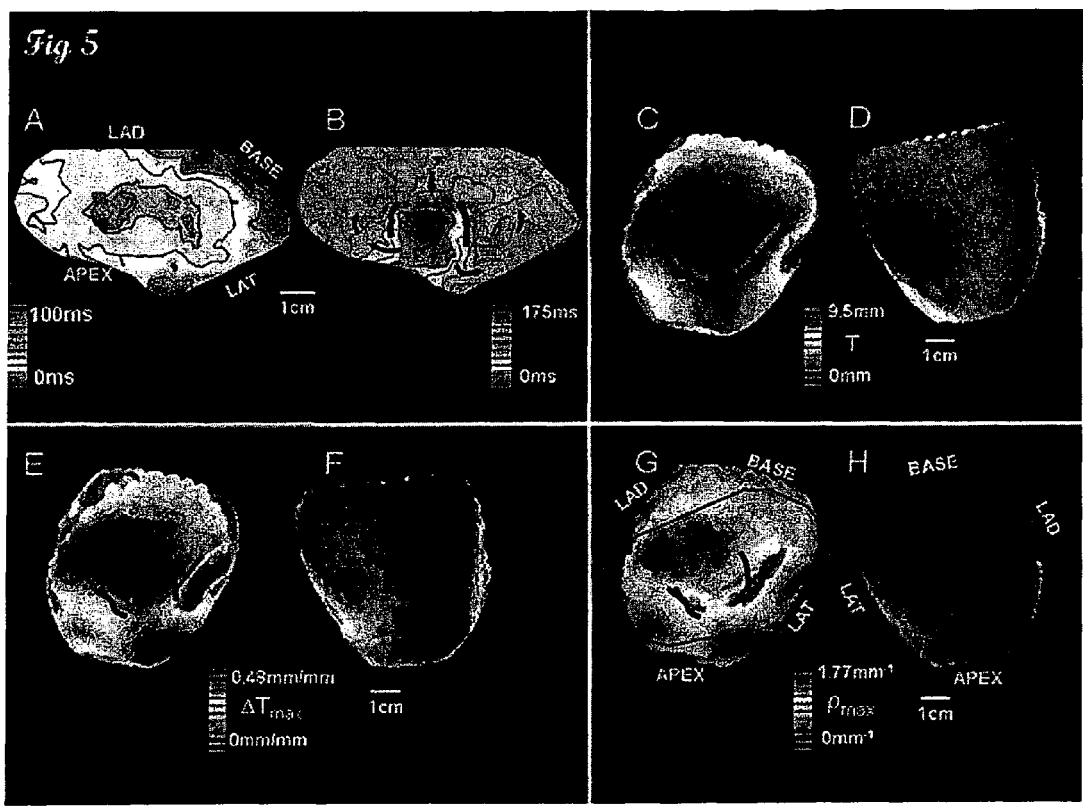
FIG. 5 illustrates BZ maps for a postinfarction canine experiment in which sustained reentrant tachycardia was inducible by extrastimulation, in accordance with an embodiment of the disclosed subject matter.
Figure 6:
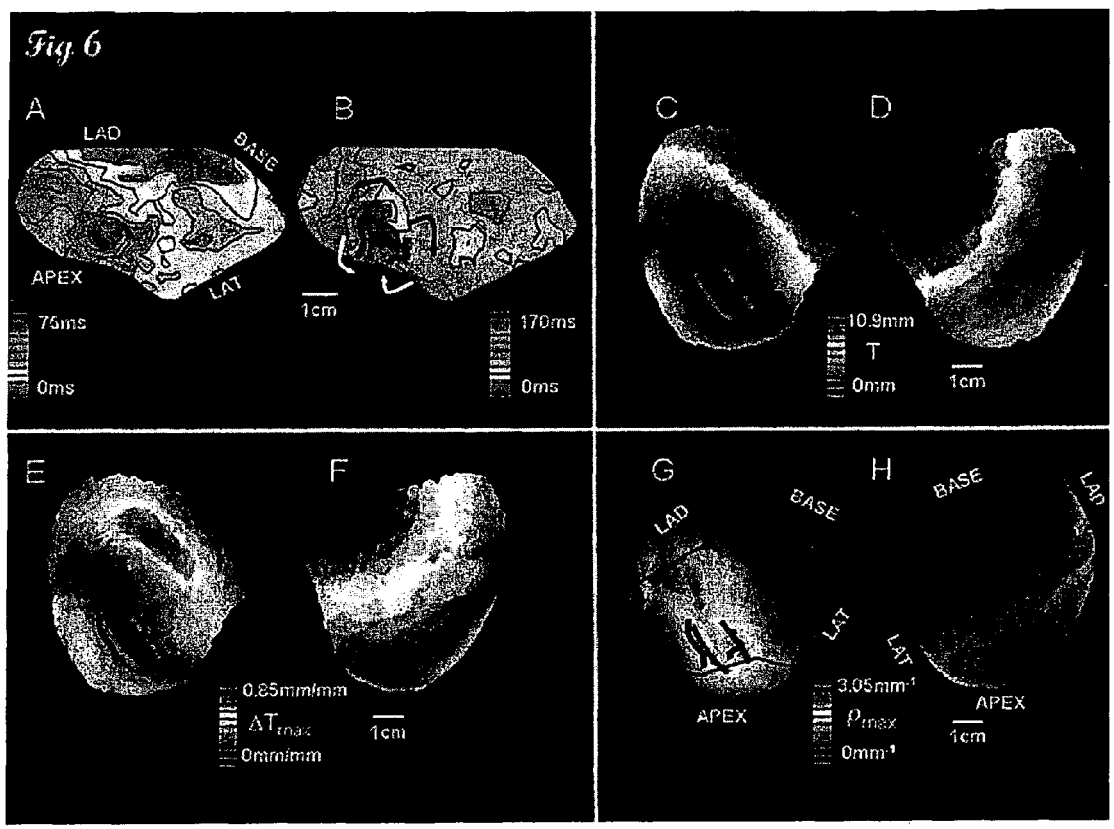
FIG. 6 illustrates BZ maps for a postinfarction canine experiment in which only nonsustained reentrant tachycardia was inducible, in accordance with an embodiment of the disclosed subject matter. Panels are the same as in FIG. 5. The figure shows that a smaller isthmus area is detected in accordance with that which would be expected in the case of inducible nonsustained reentrant ventricular tachycardia only.

Activation mapping and analysis of infarct depth after MR image measurement is shown for an experiment with only inducible sustained reentrant ventricular tachycardia (FIG. 5) and an experiment with only inducible nonsustained reentrant tachycardia (FIG. 6). Sinus rhythm and ventricular tachycardia activation maps are given in FIGS. 5-6 panels A-B. The thickness map is given in panels C-D, maximum gradient in panels E-F, and maximum estimated curvature in panels G-H. On the curvature maps (panels G), multielectrode array position during electrogram recording is noted in red outline. Reentrant tachycardia is caused by a double-loop reentrant circuit in each experiment (FIGS. 5-6B) with relatively slow and late sinus rhythm activation at the isthmus region (FIGS. 5-6A).

The thinnest tissue occurs along a band oriented in the direction between the isthmus entrance and exit (FIGS. 5-6C). Largest $\Delta T_{max}$ occurs at the lateral edges of the thin tissue region where functional block lines form, and also elsewhere along the edge of the BZ (FIGS. 5-6E-F). The maximum degree of curvature $\rho_{max}$ is coincident with the locations where BZ thickness is minimal and the BZ thickness spatial gradient is maximal, and actual block (black lines) approximately collocate with these points of maximum curvature (gray lines) (FIGS. 5-6G, also shown overlapped in panels C and E). The predicted pathway is wider and the degree of curvature at both the lateral edges and the ends of the isthmus location is less in the sustained versus the nonsustained experiment (FIGS. 5-6).

Figure 7:
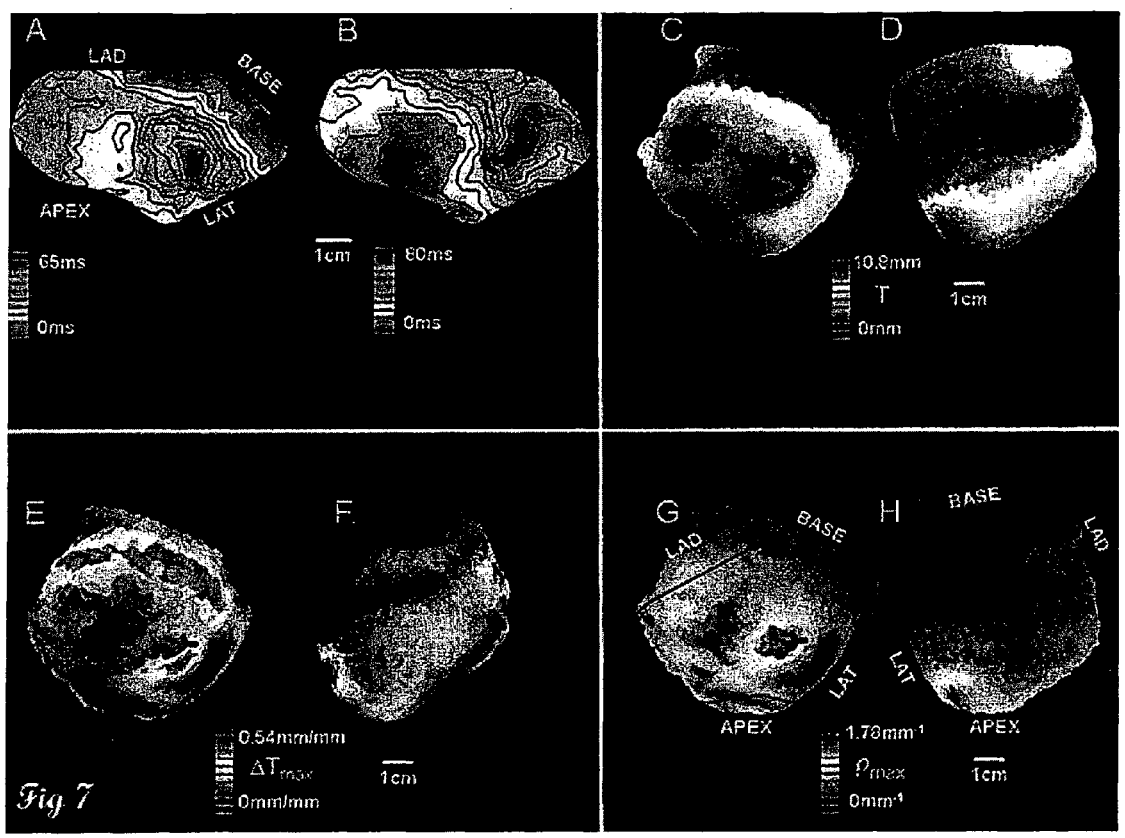
FIG. 7 illustrates BZ maps for a postinfarction canine experiment in which a reentrant circuit was not mappable although ventricular tachycardia was induced, in accordance with an embodiment of the disclosed subject matter. Panels are the same as in FIG. 5. Note isochronal spacing is ~5 ms in the sinus rhythm and ventricular tachycardia activation maps, Panels A-B. The figure shows that no potential isthmus area was detected in accordance with that which would be expected for a case in which the ventricular tachycardia was of nonreentrant origin.

Activation mapping and analysis of infarct depth after MR image measurement is shown for an experiment with no mappable reentrant tachycardia (FIG. 7). The panel labels correspond to those in FIGS. 5-6. The isochronal spacing in the activation maps of FIGS. 7A-B is 5 ms to show detail in the conduction pattern. The region of thinnest BZ with large $\rho_{max}$ at a border (FIGS. 7C,G) had slow and late sinus rhythm activation (FIG. 7A). During tachycardia, which lacked a complete circuit on the mapping grid (FIG. 7B), block occurred at the location of maximum estimated wavefront curvature (FIG. 7G). However, as predicted from FIG. 7G, only a single short functional block line, rather than two parallel lines, was present during tachycardia (FIG. 7B). Furthermore, the region of thinnest BZ at the epicardial surface (FIG. 7C) was small compared to corresponding regions in sustained and nonsustained reentry experiments (FIGS. 5-6C). MRI-generated reconstruction in this experiment (not shown) suggested that viable pathways of midmyocardial tissue may have provided a closed loop for reentry that would not be entirely mappable from the surface.

Summary Statistics

In sum, during tachycardia, the reentry isthmus overlapped the thinnest BZ region and was aligned with its long axis (FIGS. 4-6B,C). In FIG. 8, the overlap of estimated and actual block line location is shown for the six experiments with mappable double-loop reentry. The estimated ablation line (dashed) overlapped the actual isthmus width by a mean of 91.8±4.6%. The mean distance between actual and estimated block line location was 6.5±3.7 mm. The model equations were useful to detect the isthmus location with a sensitivity of 75.0±5.7% and a specificity of 97.2±0.7%. There were no statistical differences between measurements of thickness made using histologic technique as compared with MRI, thus validating the use of MRI technology for estimating BZ thickness in this system.

Table 1, below, shows the statistical variables and can be summarized as follows. The mean thickness of the BZ was much less within the isthmus location compared with outside the isthmus (231±140 μm versus 1440±770 μm; $p<0.001$).

The maximum degree of wavefront curvature ($\rho_{max}$) was 1.63±0.45 mm$^{-1}$ at block line locations, signifying that block would be expected to occur since the value was above 1.0. Mean $\rho_{max}$ was less at entrance and exit points but still relatively high (0.71±10.18 mm$^{-1}$) which suggests that conduction velocity would tend to slow at these locations. Mean $\rho_{max}$ was least elsewhere in the circuit pathway (0.33±0.13 mm$^{-1}$), which suggests that relatively rapid conduction velocity would occur in these areas.

The means were significantly different (p<0.001). The measured conduction velocities are in agreement with the calculations of $\rho_{max}$. The mean conduction velocity at entrance and exit points during tachycardia (0.32±0.05 mm/ms) was slower than elsewhere in the circuit (0.42±10.13 mm/ms). The areas of the circuit with minimal $\Delta T_{max}$ had significantly faster conduction velocity as compared with the circuit as a whole (0.64±0.16 mm/ms; p<0.001). As compared with sustained tachycardia, in nonsustained tachycardia experiments there was greater $\rho_{max}$ at block line locations and entrance-exit points, slower conduction velocity at entrance and exit points, and the BZ was thicker outside the isthmus. The thicker mean BZ away from the isthmus in nonsustained experiments likely resulted in a larger $\Delta T_{max}$ at the isthmus boundary, so that $\rho_{max}$ at the boundary was increased compared with sustained experiments. The differences described in the Table for ventricular tachycardias originating from reentrant circuits with long (sustained) and short (nonsustained) duration, as well as differences originating from nonreentrant (i.e., focal) sources (FIG. 7), are measurable with the described system and are useful in planning a clinical course of treatment.

TABLE 1

Geometry-Propagation Statistics

| VT Units | $T_i$ μm | $T_o$ μm | $\rho_{max,b}$ mm$^{-1}$ | $\rho_{max,e}$ mm$^{-1}$ | $\rho_{max,o}$ mm$^{-1}$ | VT $\theta_e$ mm/ms | VT $\theta_o$ mm/ms | VT $\theta_f$ mm/ms | distance mm |
|---|---|---|---|---|---|---|---|---|---|
| All n = 6 | 231 ± 140 | 1440 ± 770 | 1.63 ± 0.45 | 0.71 ± 0.18 | 0.33 ± 0.13 | 0.32 ± 0.04 | 0.42 ± 0.13 | 0.64 ± 0.16 | 6.45 ± 3.74 |
| NS n = 2 | 226 ± 139 | 1753 ± 893 | 2.02 ± 0.42 | 0.85 ± 0.10 | 0.41 ± 0.15 | 0.25 ± 0.03 | 0.39 ± 0.09 | 0.60 ± 0.11 | 4.39 ± 1.81 |
| MS n = 4 | 233 ± 144 | 1284 ± 671 | 1.37 ± 0.24 | 0.62 ± 0.16 | 0.27 ± 0.08 | 0.35 ± 0.05 | 0.44 ± 0.15 | 0.66 ± 0.18 | 7.48 ± 4.01 |

VT = ventricular tachycardia,
NS = nonsustained tachycardia,
MS = monomorphic sustained tachycardia.
i = inner pathway,
o = outer pathway,
f = region with minimum $\Delta T_{max}$,
b = block lines,
e = ends (entrance-exit sites).
NS = nonsustained reentrant ventricular tachycardia,
MS = monomorphic sustained ventricular tachycardia.

The foregoing merely illustrates the principles of the disclosed subject matter. Various modifications and alterations to the described embodiments will be apparent to those skilled in the art in view of the teachings herein.

It will thus be appreciated that those skilled in the art will be able to devise numerous techniques which, although not explicitly described herein, embody the principles of the disclosed subject matter and are thus within the spirit and scope of the disclosed subject matter.

All publications and patents mentioned herein are hereby incorporated by reference in their entirety as if each individual publication or patent was specifically and individually indicated to be incorporated by reference. The contents of U.S. Pat. Nos. 6,236,883, 6,847,839, and 7,245,962 are expressly incorporated herein by reference. In case of conflict, the present application, including any definitions herein, will control.

I claim:

1. A method of identifying the source of reentrant ventricular tachycardia in a patient, said method comprising:
    a) obtaining one or more images of the region of the patient's heart;
    b) identifying a border zone (BZ);
    c) calculating the thickness of the BZ;
    d) constructing a three-dimensional thickness map by measuring the thickness of said border zone at multiple points so that a sufficient spatial resolution is obtained, and determining a local spatial gradient ($\Delta T$) of said thickness over two or more locations in said BZ; and
    e) using said thickness and $\Delta T$ to determine the reentry isthmus location and one or more candidate ablation sites.

2. The method of claim 1, wherein the thickness is calculated as the straight line distance between an infarct or other structurally remodeled surface to the heart surface.

3. The method of claim 1, wherein the thickness is calculated as the straight line distance between edges of the infarct or other structurally remodeled surface when that surface is three-dimensional.

4. The method of claim 1, further comprising performing ablation of said one or more candidate ablation sites.

5. The method of claim 1, wherein said patient has suffered from a myocardial infarction.

6. The method of claim 1, wherein said patient has undergone structural remodeling of the heart.

7. The method of claim 6, wherein said structural remodeling is caused by cardiac fibrosis or the presence of dense trebeculation.

8. The method of claim 1, wherein said obtaining images comprises the use of imaging technology capable of achieving 1 mm resolution or less.

9. The method of claim 8, wherein said imaging technology is magnetic resonance imaging (MRI).

10. A method for treating, preventing, and/or inhibiting postinfarction reentrant ventricular tachycardia in a patient, said method comprising:
    a) obtaining one or more images of the patient's heart;
    b) identifying a border zone (BZ);
    e) calculating the thickness of the BZ;
    d) constructing a three-dimensional thickness map by measuring the thickness of said border zone at multiple points so that a sufficient spatial resolution is obtained, and determining a local spatial gradient ($\Delta T$) of said thickness over two or more locations in said BZ;

e) using said thickness and ΔT to determine the reentry isthmus location and one or more candidate ablation sites; and f) performing ablation of said one or more candidate ablation sites.

11. The method of claim 10, wherein the thickness is calculated as the straight line distance between an infarct or other structurally remodeled surface to the heart surface.

12. The method of claim 10, wherein the thickness is calculated as the straight line distance between edges of the infarct or other structurally remodeled surface when that surface is three-dimensional.

13. The method of claim 10, wherein said patient has suffered from a myocardial infarction.

14. The method of claim 10, wherein said patient has undergone structural remodeling of the heart.

15. The method of claim 14, wherein said structural remodeling is caused by cardiac fibrosis or the presence of dense trebeculation.

16. The method of claim 10, wherein said obtaining images comprises the use of imaging technology capable of achieving 1 mm resolution or less.

17. The method of claim 16, wherein said imaging technology is magnetic resonance imaging (MRI).

18. A system for identifying the location of a candidate ablation site in a patient, the system comprising:

a) a processor, image acquisition means for obtaining images of a patient's heart operatively coupled to the processor, and a memory operatively coupled to the processor, the memory storing program instructions that when executed by the processor, cause said processor to utilize said image acquisition means for obtaining images to:

obtain images of a patient's heart;

display each image on a screen;

measure a thickness of a border zone;

determine a local spatial gradient (ΔT) of said thickness over two or more locations in said border zones;

plot said thickness and thickness gradient values on three-dimensional maps; and locate estimated positions of reentrant circuits and actual conduction block during reentrant ventricular tachycardia.

19. The system of claim 18, wherein said system further comprises analyzing means, which analyzing means operatively coupled with said image acquisition means for analyzing whether the geometry and location of reentrant circuits indicate predisposition to ventricular tachycardia in the patient.

20. The system of claim 18, wherein said patient has undergone structural remodeling of the heart.

* * * * *